US011786587B2

(12) United States Patent
Lin et al.

(10) Patent No.: US 11,786,587 B2
(45) Date of Patent: Oct. 17, 2023

(54) COMPOSITION OF SUBUNIT DENGUE VACCINE

(71) Applicant: National Cheng Kung University, Tainan (TW)

(72) Inventors: Yee-Shin Lin, Tainan (TW); Trai-Ming Yeh, Tainan (TW); Yung-Chun Chuang, Tainan (TW); Chia-Yi Yu, Tainan (TW); Hsin-Wei Chen, Miaoli County (TW); Shu-Wen Wan, Kaohsiung (TW); Shu-Ying Wang, Tainan (TW); Tzong-Shiann Ho, Tainan (TW); Dar-Bin Shieh, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 573 days.

(21) Appl. No.: 16/906,134

(22) Filed: Jun. 19, 2020

(65) Prior Publication Data

US 2020/0397884 A1 Dec. 24, 2020

Related U.S. Application Data

(60) Provisional application No. 62/863,278, filed on Jun. 19, 2019.

(51) Int. Cl.
*A61K 39/12* (2006.01)
*C12N 7/00* (2006.01)
*C07K 14/005* (2006.01)

(52) U.S. Cl.
CPC ............ *A61K 39/12* (2013.01); *C07K 14/005* (2013.01); *C12N 7/00* (2013.01); *C07K 2319/00* (2013.01); *C12N 2770/24131* (2013.01)

(58) Field of Classification Search
None
See application file for complete search history.

(56) References Cited

U.S. PATENT DOCUMENTS

2020/0397884 A1* 12/2020 Lin ........................ A61K 39/12

FOREIGN PATENT DOCUMENTS

KR 20140090502 A 7/2014
TW 201210615 A 3/2012

OTHER PUBLICATIONS

Lee et al. (Journal of Experimental Medicine. 2020; 217 (9): 1-16).*
Park et al. (Journal of Microbiology. 2022; 60 (3): 247-254).*
Kao et al. (Journal of Immunology. 2019; 203: 1909-1917).*
Idris et al. (Expert Opinion on Drug Discovery. 2021; 16 (1): 47-58).*
Chen et al.(Current Opinion in Virology. 2020; 50-58).*
Sequence alignment of SEQ ID No. 1 with Geneseq db access AYM50450 in USPgPub 2010303849 Feb. 2011.*
Alignment of SEQ ID No. 2 with Geneseq db access BEG61670 in USPgPub 2017233460; 2017.*
World Health Organization, “Dengue vaccine: WHO position paper—Jul. 2016”, Wkly Epidemiol Rec. 2016;91(30): 349-64.
Bhatt S et al., “The global distribution and burden of dengue”, Nature. Apr. 25, 2013;496(7446):504-7.
Diamond MS et al., “Molecular insight into dengue virus pathogenesis and its implications for disease control”, Cell. Jul. 30, 2015;162(3):488-92.
Katzelnick LC et al., “Dengue: Knowledge gaps, unmet needs and research priorities”, Lancet Infect Dis. Mar. 2017; 17(3):e88-e100.
Wan SW et al., “Current progress in dengue vaccines”, J Biomed Sci. 2013;20:37.
Wichmann O et al., “Live-attenuated tetravalent dengue vaccines: the needs and challenges of post-licensure evaluation of vaccine safety and effectiveness”, Vaccine. 2017; 35:5535-42.
Normile D et al., “Safety concerns derail dengue vaccination program”, Science. Dec. 22, 2017;358:1514-5.
Sridhar S“, Effect of dengue serostatus on dengue vaccine safety and efficacy”, N Engl J Med. Jul. 26, 2018:379: 327-40.
Gubler DJ et al., “Is Dengvaxia a useful vaccine for dengue endemic areas?”, BMJ. Oct. 3, 2019;367:I5710.
Kirkpatrick BD et al., “Robust and balanced immune responses to all 4 dengue virus serotypes following administration of a single dose of a live attenuated tetravalent dengue vaccine to healthy, flavivirus-naive adults”, J Infect Dis. Sep. 1, 2015;212:702.10.
Biswal S et al., “Efficiacy of a tetravalent dengue vaccine in healthy in children and adolescents”, N Engl J Med. Nov. 6, 2019;381:2009-19.
Screaton G et al., “New insights into the immunopathology and control of dengue virus infection”, Nat Rev Immunol. 2015;15(12):745-59.
Guzman MG et al., “Domain III of the envelope protein as a dengue vaccine target”, Expert Rev Vaccines. Jan. 9, 2014;9(2):137-47.
Guzman MG et al., “Dengue”, Sep. 14, 2014, Lancet 2015;385:453-65.
Leng CH et al., “A novel dengue vaccine candidate that induces cross-neutralizing antibodies and memory immunity”, Microbes Infect. 2009;11(2):288-95.
Chen HW et al., “A consensus envelope protein domain III can induce neutralizing antibody responses against serotype 2 of dengue virus in non-human primates”, Mar. 1, 2013, Arch Virol. 2013;158(7):1523-31.

(Continued)

*Primary Examiner* — Shanon A. Foley
(74) *Attorney, Agent, or Firm* — Lippes Mathias LLP

(57) ABSTRACT

The present invention relates to a composition of subunit dengue vaccine comprising a fusion protein of conjugating or connecting delta C nonstructural protein 1 (NS1ΔC or truncated NS1ΔC) to at least one polypeptides of NS3c (or truncated NS3c) and/or consensus envelope protein domain III (cEDIII), thereby enhancing better protection against DENV challenge and alleviating associated pathological effects.

9 Claims, 30 Drawing Sheets
(2 of 30 Drawing Sheet(s) Filed in Color)
Specification includes a Sequence Listing.

(56) References Cited

OTHER PUBLICATIONS

Flamand M et al., "Dengue virus type 1 nonstructural glycoprotein NS1 is secreted from mammalian cells as a soluble hexamer in a glycosylation-dependent fashion", J Virol., Jul. 1999;73(7):6104-10.
Muller DA et al., "The flavivirus NS1 protein: Molecular and structural biology, immunology, role in pathogenesis and application as a diagnostic biomarker", Antiviral Res. 2013;98(2):192-208.
Adikari TN et al., "Dengue NS1 antigen contributes to disease severity by inducing interleukin (IL)-10 by monocytes", Clin Exp Immunol. 2016;184(1):90-100.
Malavige GN, et al., "Pathogenesis of vascular leak in dengue virus infection", Immunology. 2017;151(3):261-9.
Beatty PR et al., "Dengue virus NS1 triggers endothelial permeability and vascular leak that is prevented by NS1 vaccination", Sci Transl Med., Sep. 9, 2015;7:304ra141.
Modhiran N et al., "Dengue virus NS1 protein activates cells via Toll-like receptor 4 and disrupt endothelial cell monolayer integrity", Sci Transl Med., Sep. 9, 2015;7(304):304ra142.
Puerta-Guardo H et al., "Dengue virus NS1 disrupts the endothelial glycocalyx, leading to hyperpermeability", PLoS Pathog., Jul. 14, 2016;12(7):e1005738.
Chen HR et al., "Macrophage migration inhibitory factor is critical for dengue NS1-induced endothelial glycocalyx and hyperpermeability. PLoS Pathog", Apr. 27, 2018;14(4):e1007033.
Chen HR et al., "Dengue virus nonstructural protein 1 induces vascular leakage through macrophage migration inhibitory factor and autophagy", PLoS Negl Trop Dis., Jul. 13, 2016;10(7):e0004828.
Chao CH et al., "Dengue virus nonstructural protein 1 activates platelets via Toll-like receptor 4, leading to thrombocytopenia and hemorrhage", PLoS Pathog., Apr. 22, 2019;15(4):e1007625.
Halstead SB, "Identifying protective dengue vaccines: Guide to mastering an empirical process", Vaccine 31(2013)4501-4507.
Amorin JH et al., "The dengue virus non-structural 1 protein: risk and benefits", Virus Res. 18(2014)53-60.
Glasner DR et al., "The good, the bad, and the shocking: The multiple roles of dengue virus nonstructural protein 1 in protection and pathogenesis", Annu Rev Virol. Sep. 29, 2018; 5:227-53.
Lin CF et al., "Generation of IgM anti-platelet autoantibody in dengue patients", J Med Virol. 2001;63(2):143-9.
Lin CF et al., "Antibodies from dengue patient sera cross-react with endothelial cells and induce damage", J Med Virol. 2003;69(1):82-90.
Lin CF et al., "Expression of cytokine, chemokine, and adhesion molecule during endothelial cell activation induced by antibodies against dengue virus nonstructural protein 1", J Immunol. 2005;174:395-403.
Lin YS et al., "Molecular mimicry between virus and host and its implications for dengue disease pathogenesis", Exp Biol. Med. (Maywood) 2011; 236(5):515-23.
Chen CL et al., "Anti-dengue virus nonstructural protein 1 antibodies cause NO-mediated endothelial cell apoptosis via ceramide-regulated GSK-3b and NF-kB activation", J Immunol. 2013;191:1744-52.
Cheng HJ et al., "Proteomic analysis of endothelial cell autoantigens recognized by anti-dengue virus nonstructural protein 1 antibodies", Exp Biol Med. (Maywood) 2009;234(1):63-73.
Chen MC et al., "Deletion of the C-terminal region of dengue virus nonstructural protein 1 (NS1) abolishes anti-NS1-mediated platelet dysfunction and bleeding tendency", J Immunol. 2009;183(3):1797-803.
Wan SW et al., "Protection against dengue virus infection in mice by administation of antibodies against modified nonstructural protein 1", PLoS One., Mar. 2014;9(3):e92495.
Wan SW et al., "Therapeutic effects of monoclonal antibody against dengue virus NS1 in a STAT1 knockout mouse model of dengue infection", J Immunol. 2017;199:2834-44.
Kao YS et al., "Combination of modified NS1 and NS3 as a novel vaccine strategy against dengue virus infection", J Immunol. 2019;203:1909-17.
Chin JF et al., "The envelope glycoprotein domain III of dengue virus serotypes 1 and 2 inhibit virus entry", Microbes Infect. 2007;9(1):1-63.
Gromowski GD et al., "Characterization of an antigenic site that contains a dominant, type-specific neutralization determinant on the envelope protein domain III (ED3) of dengue 2 virus", Virology. 2007; 366(2):349-60.
Wahala WM et al., "Dengue virus neutralization by human immune sera: role of envelope protein domain III-reactive antibody", Virology. 2009; 392(1):103-13.
Coller BA et al., "The development of recombinant subunit envelope-based vaccine to protect against dengue virus induced disease", Vaccine. 2011; 29(42):7267-75.
Chen J et al., "Activation of TLR2 and TLR6 by dengue NS1 protein and its implications in the immunopathogenesis of dengue virus infection", PLoS Pathog., Jul. 30, 2015;11:e1005053.
Pang EL et al., "Towards development of a universal dengue vaccine—how close are we?", Asian Pac J Trop Med. 2017;10:220-8.
Wen J et al., "Dengue virus-reactive CD8+T cells mediate cross-protection against subsequent Zika virus challenge", Nat Commun. 2017;8:1459.
Klein DE et al., "Structure of a dengue virus envelope protein late-stage fusion intermediate", J Virol., Feb. 2013;87(4):2287-93.
Kuhn RJ et al., "Structure of dengue virus: implications for flavivirus organization, maturation, and fusion", Cell. 2002;108(5):717-25.
Chuang YC et al., "Macrophage migration inhibitory factor induced by dengue virus infection increases vascular permeability", Cytokine. 2011;54222-31.
Wan SW et al., "C-terminal region of dengue virus nonstructural protein 1 is involved in endothelial cell cross-reactivity via molecular mimicry", Am J Infect Dis. 2008;4(1):85-91.
Han Lee, "Protection of Anti-Dengue Virus Nonstructural Protein 1 Antibodies in the Wild Type and Humanized Mouse Models," Master Thesis, National Cheng Kung University, R.O.C., Jul. 30, 2014.
Monika Simmons et al., "Recombinant Dengue 2 Virus NS3 Helicase Protein Enhances Antibody and T-Cell Response of Purified Inactivated Vaccine," PLoS One, p. 1-16, Apr. 1, 2016.
Hong-Jyun Huang et al., A novel chimeric dengue vaccine candidate composed of consesnus envelope protein domain III fused to C-terminal-modified NS1 protein, Vaccine, Apr. 2022, p. 2299-2310, V 40 I 15, Elsevier.
Ashok Kumar Srivastava et al., Mice immunized with a dengue type 2 virus E and NS1 fusion protein made in *Escherichia coli* are protected against lethal dengue virus infection, Vaccine, p. 1251-1258, V 13 I 13, Elsevier.

* cited by examiner

| cEDIII | NS1ΔC | + | NS3c |

| cEDIII | Linker-1 | NS1ΔC | + | NS3c |

| cEDIII | truncated NS1ΔC | + | truncated NS3 |

| cEDIII | Linker-1 | truncated NS1ΔC | + | truncated NS3 |

| cEDIII | NS1ΔC | NS3c |

| cEDIII | Linker-1 | NS1ΔC | NS3c |

| cEDIII | NS1ΔC | Linker-2 | NS3c |

| cEDIII | Linker-1 | NS1ΔC | Linker-2 | NS3c |

| cEDIII | truncated NS1ΔC | truncated NS3 |
|---|---|---|

| cEDIII | Linker-1 | truncated NS1ΔC | truncated NS3 |
|---|---|---|---|

| cEDIII | truncated NS1ΔC | Linker-2 | truncated NS3 |
|---|---|---|---|

| cEDIII | Linker-1 | truncated NS1ΔC | Linker-2 | truncated NS3 |
|---|---|---|---|---|

| NS1ΔC | cEDIII |   +   | NS3c |

| NS1ΔC | Linker-1 | cEDIII |   +   | NS3c |

| truncated NS1ΔC | cEDIII |   +   | truncated NS3 |

| truncated NS1ΔC | Linker-1 | cEDIII |   +   | truncated NS3 |

| NS1ΔC | cEDIII | NS3c |

| NS1ΔC | Linker-1 | cEDIII | NS3c |

| NS1ΔC | cEDIII | Linker-2 | NS3c |

| NS1ΔC | Linker-1 | cEDIII | Linker-2 | NS3c |

| truncated NS1ΔC | cEDIII | truncated NS3 |

| truncated NS1ΔC | Linker-1 | cEDIII | truncated NS3 |

| truncated NS1ΔC | cEDIII | Linker-2 | truncated NS3 |

| truncated NS1ΔC | Linker-1 | cEDIII | Linker-2 | truncated NS3 |

| truncated NS1ΔC | truncated NS3 |

| truncated NS1ΔC | Linker-1 | truncated NS3 |

| truncated NS3 | truncated NS1ΔC |

| truncated NS3 | Linker-1 | truncated NS1ΔC |

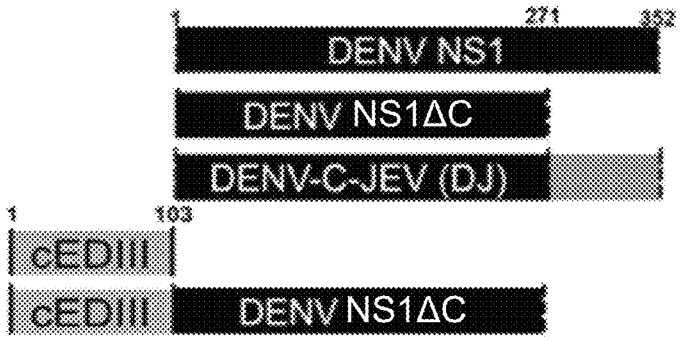
FIG. 9A
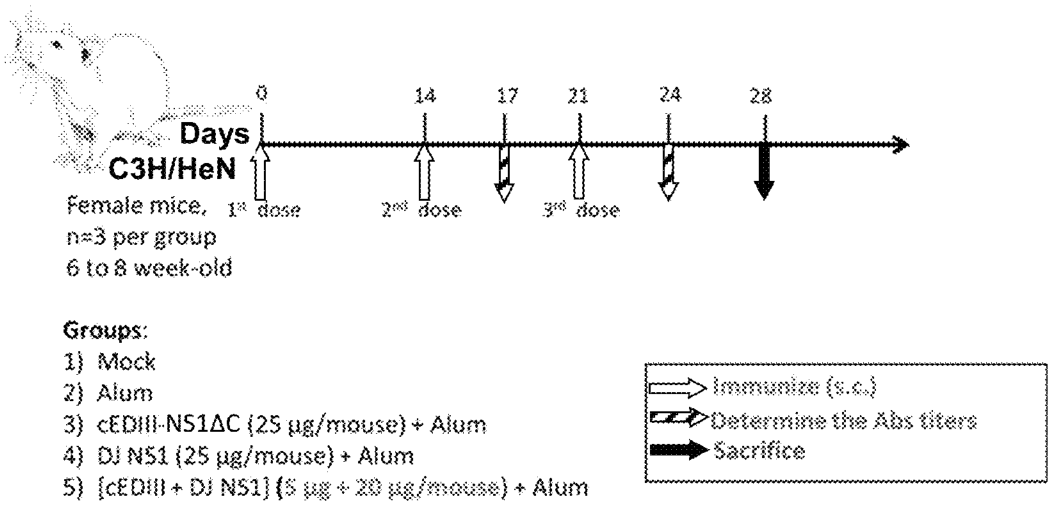
FIG. 9B
| Times of immunization | Antibody titer (× $10^3$) | | | | | | | | | | | |
|---|---|---|---|---|---|---|---|---|---|---|---|---|
| | DJ NS1 serum (25 μg) | | **cEDIII-NS1ΔC serum (25 μg)** | | | | | | cEDIII + DJ NS1 serum (5 μg + 20 μg) | | | |
| | Anti-DJ NS1 | | Anti-cEDIII | | Anti-DJ NS1 | | Anti-NS1 ΔC | | Anti-cEDIII | | Anti-DJ NS1 | |
| | IgM | IgG | IgM | IgG | IgM | IgG | IgM | IgG | IgM | IgG | IgM | IgG |
| 2nd | $2^1$ | $2^1$ | $2^3$ | $2^3$ | $2^3$ | $2^3$ | $2^4$ | $2^4$ | $2^4$ | $2^4$ | $2^4$ | $2^4$ |
| 3rd | $2^2$ | $2^4$ | $2^5$ | $2^7$ | $2^6$ | $2^7$ | $2^6$ | $2^7$ | $2^5$ | $2^6$ | $2^4$ | $2^6$ |
FIG. 9C

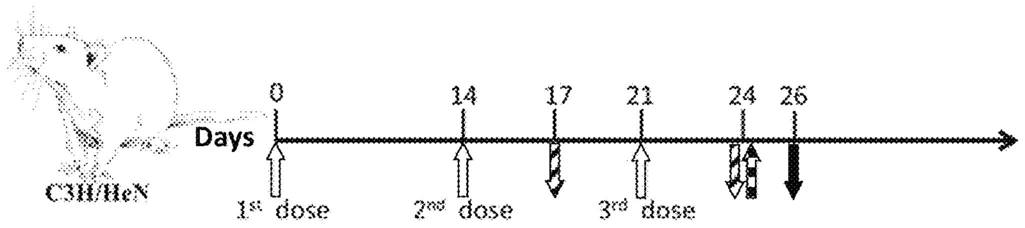

Groups:
1) Mock
2) Mock + DENV1
3) Alum + DENV1
4) cEDIII-NS1ΔC (25 μg/mouse) + Alum + DENV1
5) Mock + DENV2
6) Alum + DENV2
7) cEDIII-NS1ΔC (25 μg/mouse) + Alum + DENV2
8) Mock + DENV3
9) Alum + DENV3
10) cEDIII-NS1ΔC (25 μg/mouse) + Alum + DENV3
11) Mock + DENV4
12) Alum + DENV4
13) cEDIII-NS1ΔC (25 μg/mouse) + Alum + DENV4

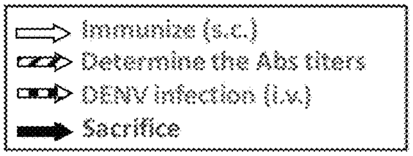

FIG. 12A

| Times of Immunization | Antibody titer (x $10^3$) | | | | | | | | | | | | | | | |
|---|---|---|---|---|---|---|---|---|---|---|---|---|---|---|---|---|
| | DENV1 | | | | DENV2 | | | | DENV3 | | | | DENV4 | | | |
| | Anti-cEDIII | | Anti-NS1ΔC | | Anti-cEDIII | | Anti-NS1ΔC | | Anti-cEDIII | | Anti-NS1ΔC | | Anti-cEDIII | | Anti-NS1ΔC | |
| | IgG | IgM | IgG | IgM | IgG | IgM | IgG | IgM | IgG | IgM | IgG | IgM | IgG | IgM | IgG | IgM |
| 2nd | $2^4$ | $2^3$ | $2^4$ | $2^4$ | $2^5$ | $2^3$ | $2^4$ | $2^3$ | $2^5$ | $2^3$ | $2^5$ | $2^4$ | $2^5$ | $2^2$ | $2^5$ | $2^3$ |
| 3rd | $2^7$ | $2^3$ | $2^7$ | $2^4$ | $2^8$ | $2^4$ | $2^8$ | $2^5$ | $2^8$ | $2^3$ | $2^8$ | $2^5$ | $2^8$ | $2^3$ | $2^8$ | $2^5$ |

FIG. 12B

- Groups:
1. Mock (2% FBS RPMI medium)
2. Mock + DENV2
3. Alum + DENV2
4. His-ΔC NS1f-NS3cf-Strep + Alum + DENV2
5. His-ΔC NS1f-cEDIII-NS3cf-Strep + Alum + DENV2
- Infection with DENV2 454009A $1\times10^8$ PFU/mouse (intravenous)
- Immunize with fusion protein 25 µg/mouse
- Protein purified from Drosophila S2 cells

DENV2

SEQUENCE LISTING

```
<160> NUMBER OF SEQ ID NOS: 6

<210> SEQ ID NO 1
<211> LENGTH: 100
<212> TYPE: PRT
<213> ORGANISM: Artificial sequence
<220> FEATURE:
<223> OTHER INFORMATION: cEDIII polypeptide of dengue virus

<400> SEQUENCE: 1

Lys Gly Met Ser Tyr Ala Met Cys Thr Gly Lys Phe Lys Leu Glu Lys
                5                   10                  15

Glu Val Ala Glu Thr Gln His Gly Thr Ile Leu Ile Lys Val Lys Tyr
            20                  25                  30

Glu Gly Asp Gly Ala Pro Cys Lys Ile Pro Phe Glu Ile Gln Asp Val
        35                  40                  45

Glu Lys Lys His Val Asn Gly Arg Leu Ile Thr Ala Asn Pro Ile Val
    50                  55                  60

Thr Asp Lys Glu Ser Pro Val Asn Ile Glu Ala Glu Pro Pro Phe Gly
65                  70                  75                  80

Asp Ser Tyr Ile Val Ile Gly Val Gly Asp Lys Ala Leu Lys Leu Asn
                85                  90                  95

Trp Phe Lys Lys
            100


<210> SEQ ID NO 2
<211> LENGTH: 275
<212> TYPE: PRT
<213> ORGANISM: Artificial sequence
<220> FEATURE:
<223> OTHER INFORMATION: delta C NS1 (NS1LGC) of dengue virus

<400> SEQUENCE: 2

Met Val Gln Ala Asp Ser Gly Cys Val Val Ser Trp Lys Asn Lys Glu
                5                   10                  15
```

-continued

```
Leu Lys Cys Gly Ser Gly Ile Phe Ile Thr Asp Asn Val His Thr Trp
            20                  25                  30

Thr Glu Gln Tyr Lys Phe Gln Pro Glu Ser Pro Ser Lys Leu Ala Ser
        35                  40                  45

Ala Ile Gln Lys Ala His Glu Glu Gly Ile Cys Gly Ile Arg Ser Val
    50                  55                  60

Thr Arg Leu Glu Asn Leu Met Trp Lys Gln Ile Thr Pro Glu Leu Asn
65                  70                  75                  80

His Ile Leu Ser Glu Asn Glu Val Lys Leu Thr Ile Met Thr Gly Asp
                85                  90                  95

Ile Lys Gly Ile Met Gln Ala Gly Lys Arg Ser Leu Gln Pro Gln Pro
            100                 105                 110

Thr Glu Leu Lys Tyr Ser Trp Lys Thr Trp Gly Lys Ala Lys Met Leu
        115                 120                 125

Ser Thr Glu Ser His Asn Gln Thr Phe Leu Ile Asp Gly Pro Glu Thr
    130                 135                 140

Ala Glu Cys Pro Asn Thr Asn Arg Ala Trp Asn Ser Leu Glu Val Glu
145                 150                 155                 160

Asp Tyr Gly Phe Gly Val Phe Thr Thr Asn Ile Trp Leu Lys Leu Arg
                165                 170                 175

Glu Lys Gln Asp Val Phe Cys Asp Ser Lys Leu Met Ser Ala Ala Ile
            180                 185                 190

Lys Asp Asn Arg Ala Val His Ala Asp Met Gly Tyr Trp Ile Glu Ser
        195                 200                 205

Ala Leu Asn Asp Thr Trp Lys Ile Glu Lys Ala Ser Phe Ile Glu Val
    210                 215                 220

Lys Ser Cys His Trp Pro Lys Ser His Thr Leu Trp Ser Asn Gly Val
225                 230                 235                 240

Leu Glu Ser Glu Met Ile Ile Pro Lys Asn Phe Ala Gly Pro Val Ser
                245                 250                 255

Gln His Asn Tyr Arg Pro Gly Tyr His Thr Gln Thr Ala Gly Pro Trp
            260                 265                 270

His Leu Gly
        275


<210> SEQ ID NO 3
<211> LENGTH: 448
<212> TYPE: PRT
<213> ORGANISM: Artificial sequence
<220> FEATURE:
<223> OTHER INFORMATION: NS3c protein of dengue virus

<400> SEQUENCE: 3

Ser Ile Glu Asp Asn Pro Glu Ile Glu Asp Asp Ile Phe Arg Lys Arg
                5                   10                  15

Lys Leu Thr Ile Met Asp Leu His Pro Gly Ala Gly Lys Thr Lys Arg
            20                  25                  30

Tyr Leu Pro Ala Ile Val Arg Glu Ala Ile Lys Arg Gly Leu Arg Thr
        35                  40                  45

Leu Ile Leu Ala Pro Thr Arg Val Val Ala Ala Glu Met Glu Glu Ala
    50                  55                  60

Leu Arg Gly Leu Pro Ile Arg Tyr Gln Thr Pro Ala Ile Arg Ala Glu
65                  70                  75                  80

His Thr Gly Arg Glu Ile Val Asp Leu Met Cys His Ala Thr Phe Thr
                85                  90                  95
```

-continued

```
Met Arg Leu Leu Ser Pro Val Arg Val Pro Asn Tyr Asn Leu Ile Ile
            100                 105                 110

Met Asp Glu Ala His Phe Thr Asp Pro Ala Ser Ile Ala Ala Arg Gly
        115                 120                 125

Tyr Ile Ser Thr Arg Val Glu Met Gly Glu Ala Ala Gly Ile Phe Met
    130                 135                 140

Thr Ala Thr Pro Pro Gly Ser Arg Asp Pro Phe Pro Gln Ser Asn Ala
145                 150                 155                 160

Pro Ile Met Asp Glu Glu Arg Glu Ile Pro Glu Arg Ser Trp Ser Ser
                165                 170                 175

Gly His Glu Trp Val Thr Asp Phe Lys Gly Lys Thr Val Trp Phe Val
            180                 185                 190

Pro Ser Ile Lys Ala Gly Asn Asp Ile Ala Ala Cys Leu Arg Lys Asn
        195                 200                 205

Gly Lys Lys Val Ile Gln Leu Ser Arg Lys Thr Phe Asp Ser Glu Tyr
    210                 215                 220

Val Lys Thr Arg Thr Asn Asp Trp Asp Phe Val Val Thr Thr Asp Ile
225                 230                 235                 240

Ser Glu Met Gly Ala Asn Phe Lys Ala Glu Arg Val Ile Asp Pro Arg
                245                 250                 255

Arg Cys Met Lys Pro Val Ile Leu Thr Asp Gly Glu Glu Arg Val Ile
            260                 265                 270

Leu Ala Gly Pro Met Pro Val Thr His Ser Ser Ala Ala Gln Arg Arg
        275                 280                 285

Gly Arg Ile Gly Arg Asn Pro Lys Asn Glu Asn Asp Gln Tyr Ile Tyr
    290                 295                 300

Met Gly Glu Pro Leu Glu Asn Asp Glu Asp Cys Ala His Trp Lys Glu
305                 310                 315                 320

Ala Lys Met Leu Leu Asp Asn Ile Asn Thr Pro Glu Gly Ile Ile Pro
                325                 330                 335

Ser Met Phe Glu Pro Glu Arg Glu Lys Val Asp Ala Ile Asp Gly Glu
            340                 345                 350

Tyr Arg Leu Arg Gly Glu Ala Arg Lys Thr Phe Val Asp Leu Met Arg
        355                 360                 365

Arg Gly Asp Leu Pro Val Trp Leu Ala Tyr Arg Val Ala Ala Glu Gly
    370                 375                 380

Ile Asn Tyr Ala Asp Arg Arg Trp Cys Phe Asp Gly Ile Lys Asn Asn
385                 390                 395                 400

Gln Ile Leu Glu Glu Asn Val Glu Val Glu Ile Trp Thr Lys Glu Gly
                405                 410                 415

Glu Arg Lys Lys Leu Lys Pro Arg Trp Leu Asp Ala Arg Ile Tyr Ser
            420                 425                 430

Asp Pro Leu Ala Leu Lys Glu Phe Lys Glu Phe Ala Ala Gly Arg Lys
        435                 440                 445
```

<210> SEQ ID NO 4
<211> LENGTH: 101
<212> TYPE: PRT
<213> ORGANISM: Artificial sequence
<220> FEATURE:
<223> OTHER INFORMATION: Mimic DENV2 cEDIII (strain 16681, 295-395 a.a.)

<400> SEQUENCE: 4

```
Lys Gly Met Ser Tyr Ser Met Cys Thr Gly Lys Phe Lys Val Val Lys
                  5                  10                  15
```

```
Glu Ile Ala Glu Thr Gln His Gly Thr Ile Val Ile Arg Val Gln Tyr
            20                  25                  30

Glu Gly Asp Gly Ser Pro Cys Lys Ile Pro Phe Glu Ile Met Asp Leu
        35                  40                  45

Glu Lys Arg His Val Leu Gly Arg Leu Ile Thr Val Asn Pro Ile Val
    50                  55                  60

Thr Glu Lys Asp Ser Pro Val Asn Ile Glu Ala Glu Pro Pro Phe Gly
65                  70                  75                  80

Asp Ser Tyr Ile Ile Ile Gly Val Glu Pro Gly Gln Leu Lys Leu Asn
                85                  90                  95

Trp Phe Lys Lys Gly
            100


<210> SEQ ID NO 5
<211> LENGTH: 154
<212> TYPE: PRT
<213> ORGANISM: Artificial sequence
<220> FEATURE:
<223> OTHER INFORMATION: truncated delta C NS1 (DENV2 strain 16681, 91-
      244 a.a.)

<400> SEQUENCE: 5

Gly Asp Ile Lys Gly Ile Met Gln Ala Gly Lys Arg Ser Leu Arg Pro
                5                   10                  15

Gln Pro Thr Glu Leu Lys Tyr Ser Trp Lys Thr Trp Gly Lys Ala Lys
            20                  25                  30

Met Leu Ser Thr Glu Ser His Asn Gln Thr Phe Leu Ile Asp Gly Pro
        35                  40                  45

Glu Thr Ala Glu Cys Pro Asn Thr Asn Arg Ala Trp Asn Ser Leu Glu
    50                  55                  60

Val Glu Asp Tyr Gly Phe Gly Val Phe Thr Thr Asn Ile Trp Leu Lys
65                  70                  75                  80

Leu Lys Glu Lys Gln Asp Val Phe Cys Asp Ser Lys Leu Met Ser Ala
                85                  90                  95

Ala Ile Lys Asp Asn Arg Ala Val His Ala Asp Met Gly Tyr Trp Ile
            100                 105                 110

Glu Ser Ala Leu Asn Asp Thr Trp Lys Ile Glu Lys Ala Ser Phe Ile
        115                 120                 125

Glu Val Lys Asn Cys His Trp Pro Lys Ser His Thr Leu Trp Ser Asn
    130                 135                 140

Gly Val Leu Glu Ser Glu Met Ile Ile Pro
145                 150


<210> SEQ ID NO 6
<211> LENGTH: 91
<212> TYPE: PRT
<213> ORGANISM: Artificial sequence
<220> FEATURE:
<223> OTHER INFORMATION: truncated NS3c (DENV3 strain D3/H/IMTSSA-
      SRI/2000/1266, 367-457 a.a.)

<400> SEQUENCE: 6

Lys Ala Gly Asn Asp Ile Ala Asn Cys Leu Arg Lys Asn Gly Lys Lys
                5                   10                  15

Val Ile Gln Leu Ser Arg Lys Thr Phe Asp Thr Glu Tyr Gln Lys Thr
            20                  25                  30

Lys Leu Asn Asp Trp Asp Phe Val Val Thr Thr Asp Ile Ser Glu Met
        35                  40                  45
```

-continued

| | | | | | | | | | | | | | | | |
|---|---|---|---|---|---|---|---|---|---|---|---|---|---|---|---|
| Gly | Ala | Asn | Phe | Lys | Ala | Asp | Arg | Val | Ile | Asp | Pro | Arg | Arg | Cys | Leu |
| | 50 | | | | | 55 | | | | | 60 | | | | |
| Lys | Pro | Val | Ile | Leu | Thr | Asp | Gly | Pro | Glu | Arg | Val | Ile | Leu | Ala | Gly |
| 65 | | | | | 70 | | | | | 75 | | | | | 80 |
| Pro | Met | Pro | Val | Thr | Ala | Ala | Ser | Ala | Ala | Gln | | | | | |
| | | | | 85 | | | | | 90 | | | | | | |

COMPOSITION OF SUBUNIT DENGUE VACCINE

RELATED APPLICATIONS

This application claims benefit of priority from U.S. Provisional Application No. 62/863,278, filed on Jun. 19, 2019, all of which are herein incorporated by reference in their entireties.

A sequence listing is being submitted herein as an ASCII text file with the name "SP-4648-US_SEQ_LIST.txt", created on Jun. 19, 2020, with a file size of 10,038 bytes.

BACKGROUND

Field of Invention

The present invention relates a composition of subunit vaccine, and more specifically, the present invention relates to a composition of dengue recombinant subunit vaccine comprising a fusion protein of conjugating or connecting delta C nonstructural protein 1 (NS1ΔC or truncated NS1ΔC) to at least one polypeptides of NS3c (or truncated NS3c) and/or consensus envelope protein domain III (cEDIII).

Description of Related Art

Dengue virus (DENV) is the most important arthropod-borne viral disease of public health in the world (WHO, 2016). DENV is transmitted to people by the mosquitoes *Aedes aegypti* and *Aedes albopictus*, causing estimated 390 million infections annually, of which 96 million cases with apparent manifestations and 500,000 cases of dengue hemorrhagic fever or dengue shock syndrome (DHF/DSS) (Bhatt et al., 2013; Diamond and Pierson, 2015; Katzelnick et al., 2017). Up to date, transmission of DENV has been reported in more than 128 countries, primarily affecting tropics and subtropics of the Asia and Latin America regions. Therefore, the development of dengue vaccine is very important in order to control dengue disease (Wan et al., 2013).

The world first dengue vaccine Dengvaxia® (or known as CYD-TDV) had been launched by Sanofi Pasteur in December 2015; however, the safety in seronegative vaccine recipients remains a concern (Wichmann et al., 2017; Normile, 2017; Sridhar et al., 2018; Gubler and Halstead, 2019). Additional two dengue vaccines, TV003/TV005 developed by the National Institute of Allergy and Infectious Diseases (NIAID), USA, and TAK-003 developed by Takeda, are in phase III trial (Kirkpatrick et al., 2015; Biswal et al., 2019). These three vaccines are live-attenuated vaccines (Screaton et al., 2015; WHO, 2016). Due to the safety concerns of current dengue vaccination program of Dengvaxia®, other live-attenuated vaccine candidates likely face increased scrutiny (Normile, 2017). The development of improved vaccines and/or antiviral therapies against DENV remains a global public health priority.

For subunit dengue vaccine development, previous studies suggested that the envelope (E) protein is a major antigen for inducing protective antibody responses. E protein domain III (EDIII), which contains cell surface receptor recognition sites, is considered as a potential subunit vaccine target (Guzman et al., 2010). However, antibodies against E are not only neutralizing but also enhancing DENV infection through antibody-dependent enhancement (ADE) (Guzman et al., 2015). A consensus EDIII (cEDIII) immunogen has been prepared by aligning sequences from different isolates of the four DENV serotypes. Studies showed that the cEDIII elicited antibody responses to cross-neutralize the four serotypes of DENV (Leng et al., 2009). In a non-human primate study, monkeys that received the cEDIII with aluminum phosphate developed a significantly strong and long-lasting antibody response against DENV2. The specific T cell response with cytokine production was also induced and correlated with the antibody response (Chen et al., 2013).

The NS1 protein is dimerized after posttranslational modification in the lumen of the endoplasmic reticulum (ER) and is expressed on the surface of infected cells. NS1 is also secreted as a soluble, lipid-associated hexamer which becomes a major target of humoral immunity (Flamand et al., 1999; Muller and Young, 2013). Higher NS1 levels have been shown to associate with DHF and the NS1 persists for a longer duration in those with vascular leak (Adikari et al., 2016; Malavige and Ogg, 2017). Secreted NS1 can activate cells to release proinflammatory cytokines which cause cytokine storm, then contributing to vascular leakage (Beatty et al., 2015; Modhiran et al., 2015). Secreted NS1 disrupts endothelial glycocalyx which leads to hyperpermeability (Puerta-Guardo et al., 2016; Chen et al., 2016; Chen et al., 2018). Recent study showed that NS1 can also activate platelets via TLR4, leading to thrombocytopenia and hemorrhage (Chao et al., 2019). Based on these findings, there is therefore an increasing attention to focus on NS1 as a candidate for vaccine development and therapeutic strategy (Halstead, 2013; Amorim et al., 2014; Glasner et al., 2018).

However, antibodies generated against DENV NS1 recognize common epitopes on coagulation-related proteins, platelets, and endothelial cells. Previous studies of the inventors indicated that anti-DENV NS1 antibodies cross-react with human platelets as well as endothelial cells and cause their damage and dysfunction (Lin et al., 2001, 2003, 2005, 2011; Chen et al., 2013). The regions of homology between DENV NS1 and cell surface antigens are predominantly located in C-terminal amino acid residues 311-352 (Cheng et al., 2009). Deletion of the C-terminal region of NS1 to generate NS1ΔC largely reduced the cross-reactivity (Chen et al., 2009). Passive immunization with anti-NS1ΔC polyclonal or monoclonal antibodies reduced DENV-induced prolonged bleeding time, hemorrhage (Wan et al., 2014; Wan 2017). Therefore, it is necessary to determine the protective effects of cEDIII-NS1ΔC fusion protein as potential subunit vaccine candidates.

SUMMARY

An aspect of the invention provides a composition of a subunit dengue vaccine comprising a fusion protein of a delta C nonstructural protein 1 (NS1ΔC) polypeptide conjugating or connecting to at least one polypeptides of a NS3c polypeptide and/or a consensus envelope protein domain III (cEDIII), and optionally together with one or more pharmaceutically acceptable carriers and/or adjuvants.

Another aspect of the invention provides a composition of a subunit dengue vaccine comprising a NS3c polypeptide and a fusion protein of consensus envelope protein domain III and delta C nonstructural protein 1 (cEDIII-NS1ΔC), and optionally together with one or more pharmaceutically acceptable carriers and/or adjuvants.

A further aspect of the invention provides a composition of a subunit dengue vaccine comprising a fusion protein of NS1ΔC and NS3c, optionally together with one or more pharmaceutically acceptable carriers and/or adjuvants.

In view of the foregoing aspect, the invention provides a composition of subunit dengue vaccine, which comprises a fusion protein of a NS1ΔC polypeptide conjugating or connecting to at least one polypeptides of a NS3c polypeptide and/or a cEDIII polypeptide. In this embodiment, the NS1ΔC polypeptide can be listed as SEQ ID NOs: 2 or 5, the cEDIII polypeptide can be listed as SEQ ID NOs: 1 or 4, and the NS3c polypeptide can be listed as SEQ ID NOs: 3 or 6. Moreover, the fusion protein optionally together with one or more pharmaceutically acceptable carriers and/or adjuvants.

In view of the foregoing aspect, the invention also provides a composition of subunit dengue vaccine. The composition comprises a fusion protein including a cEDIII polypeptide of SEQ ID NO: 1 and a NS1ΔC polypeptide of SEQ ID NO: 2, a NS3c polypeptide including SEQ ID NO: 3; and optionally together with one or more pharmaceutically acceptable carriers and/or adjuvants.

In an embodiment, the aforementioned fusion protein can be in an order of cEDIII-NS1ΔC from N-terminus to C-terminus. In an example, the fusion protein includes a first linker between the cEDIII polypeptide and the NS1ΔC polypeptide.

In embodiment, the fusion protein in an order of NS1ΔC-cEDIII from N-terminus to C-terminus can be conjugated to the NS3c polypeptide. In an example, a second linker can be conjugated to between the NS1ΔC polypeptide and the NS3c polypeptide.

In embodiment, the fusion protein can be in an order of NS1ΔC-cEDIII from N-terminus to C-terminus. In an example, the fusion protein can include a first linker between the cEDIII polypeptide and the NS1ΔC polypeptide.

In an embodiment, the fusion protein in an order of NS1ΔC-cEDIII from N-terminus to C-terminus can be conjugated to the NS3c polypeptide. In an example, a second linker can be conjugated to between the cEDIII polypeptide and the NS3c polypeptide.

In an embodiment, the composition of the subunit dengue vaccine can further include an adjuvant.

In view of the foregoing aspect, the invention further provides a composition of subunit dengue vaccine comprising a fusion protein of truncated NS1 polypeptide of SEQ ID NO: 5 and truncated NS3c polypeptide of SEQ ID NO: 6, and optionally together with one or more pharmaceutically acceptable carriers and/or adjuvants.

In an embodiment, the fusion protein is in an order of truncated NS1-truncated NS3c from N-terminus to C-terminus.

In an embodiment, the fusion protein includes a first linker between the truncated NS1 and the truncated NS3c polypeptide.

In an embodiment, the fusion protein is in an order of truncated NS3c-truncated NS1 from N-terminus to C-terminus.

In an embodiment, the fusion protein includes a first linker between the truncated NS1 and the truncated NS3c polypeptide.

In an embodiment, the composition further comprises a cEDIII polypeptide listed as SEQ ID NOs: 1 or 4. In this embodiment, the truncated NS1 polypeptide of the fusion protein can be optionally conjugated to the cEDIII polypeptide. In some examples, the truncated NS3c polypeptide of the fusion protein can be optionally conjugated to the cEDIII polypeptide. In other examples, the cEDIII polypeptide can be optionally conjugated between the truncated NS1 polypeptide and the truncated NS3c polypeptide.

With application to the aforementioned composition of subunit dengue vaccine, which comprises the cEDIII-NS1ΔC fusion protein and the NS3c polypeptide, or a fusion protein of truncated NS1 polypeptide and truncated NS3c polypeptide, thereby enhancing better protection against DENV challenge and alleviating associated pathological effects.

BRIEF DESCRIPTION OF THE DRAWINGS

The patent or application file contains at least one drawing executed in color. Copies of this patent or patent application publication with color drawings will be provided by Office upon request and payment of the necessary fee. The disclosure can be more fully understood by reading the following detailed description of the embodiment, with reference made to the accompanying drawings as follows.

FIGS. 9A to 9C depict the results of antibody responses induced by immunization with cEDIII-NS1ΔC, cEDIII plus DJ NS1, and DJ NS1 recombinant proteins. (FIG. 9A) The diagram shows cEDIII, NS1ΔC, DJ NS1 and a linear fusion of cEDIII-NS1ΔC recombinant proteins. (FIG. 9B) Mice were subcutaneously immunized three times with 25 μg cEDIII-NS1ΔC/mouse, 5 μg cEDIII+20 μg DJ NS1/mouse or 25 μg DJ NS1 protein/mouse with alum as adjuvant. (FIG. 9C) Mouse sera were collected and antibody titers were determined three days after second and third immunization. (n=3).

FIGS. 12A and 12B depict experimental design and antibody titers in cEDIII-NS1ΔC protein-immunized mice before different serotypes of DENV infection. (FIG. 12A) Mice were subcutaneously (s.c.) immunized three times with 25 μg/mouse of cEDIII-NS1ΔC protein mixed with alum. Mouse sera were collected and antibody titers were determined three days after 2nd and 3rd immunization. (n=2 for mock group, n=3 for DENV alone group, n=4 for DENV plus alum group and DENV plus cEDIII-NS1ΔC mixed with alum). (FIG. 12B) Mice were inoculated with $1\times10^8$ PFU of DENV1, DENV2, DENV3, and DENV4 by intravenous (i.v.) route at day 24. After 2 days post-infection, mice were assayed for prolonged bleeding time and sera were collected to determine viral titers and soluble NS1 levels as shown in FIGS. 13A-14D.

(FIG. 15A) Percentage of $CD25^+$ in $CD4^+$ T cells in response to DJ NS1 antigen stimulation. (FIG. 15B) Percentage of $CD25^+$ in $CD4^+$ T cells in response to NS3 antigen stimulation. (FIG. 15C) Percentage of $CD25^+$ in $CD8^+$ T cells in response to DJ NS1 antigen stimulation. (FIG. 15D) Percentage of $CD25^+$ in $CD8^+$ T cells in response to NS3 antigen stimulation. n=5 for DJ NS1 plus NS3 group and n=4 for other groups. The averages of each group±SD are shown. *p<0.05, p<0.01, *p<0.001, as determined by one-way ANOVA with Tukey post hoc test.

(FIG. 16A) Experimental design of CTL killing assay. Lymph node cells were collected and re-stimulated with 5 μg/ml DJ NS1 or NS3 proteins for 3 days as effector cells. (FIG. 16B) NS1-expressing L929 cells were cocultured with effector cells at E:T ratio of 20:1. After 4 h, target cells were collected and assayed for cell death by PI staining and flow cytometry. The NS1 expression levels were detected by Western blotting. (FIG. 16C) NS2B/3 with S135A was used for NS3-expressing cells, and the impaired protease activity of the mutated constructs was confirmed by analyzing the absence of NS2B3 self-processing by Western blotting. NS3-expressing L929 cells were cocultured with effector cells at E:T ratio of 20:1. After 4 h, target cells were collected and assayed for cell death by PI staining and flow cytometry. n=5 for DJ NS1 plus NS3 group and n=4 for other groups. The averages of each group±SD are shown. *p<0.05, **p<0.01, as determined by one-way ANOVA with Tukey post hoc test.

(FIG. 18A) Experimental design of mouse model of immunization is shown (n=3/group). C3H/HeN mice were inoculated i.v. with $1\times10^8$ PFU DENV2 strain 454009A at day 17. (FIG. 18B) Active immunization with DJ NS1 and NS3 reduces DENV-elicited bleeding tendency is shown. Mice were inoculated i.v. with $1\times10^8$ PFU DENV2 strain 454009A at day 17. The tail bleeding time is determined at 2 days post-infection. (FIG. 18C) Mice were sacrificed at day 19 and serum samples were collected to determine the viral titers by FFA. *p<0.05, p<0.01, *p<0.001, as determined by one-way ANOVA with Tukey post hoc test.

FIG. 21C) and bleeding time (FIG. 21D) in the DENV-infected mice.

FIG. 22C) and bleeding time (FIG. 22D) in the DENV-infected mice.

DETAILED DESCRIPTION

Figure 1A:
FIGS. 1A to 8B depict various subunits of the composition of subunit dengue vaccines according to embodiments of the present invention.
Figure 1B:
Figure 1C:
Figure 1D:
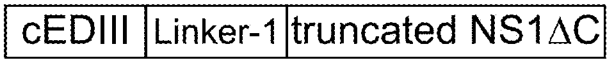
Figure 2A:
Figure 2B:
Figure 2C:
Figure 2D:
Figure 3A:
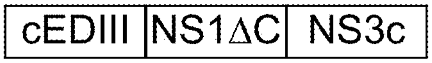
Figure 3B:
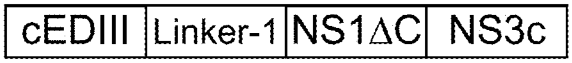
Figure 3C:
Figure 3D:
Figure 3E:
Figure 3F:
Figure 3G:
Figure 3H:
Figure 4A:
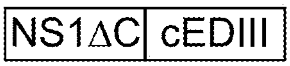
Figure 4B:
Figure 4C:
Figure 4D:
Figure 5A:
Figure 5B:
Figure 5C:
Figure 5D:
Figure 6A:
Figure 6B:
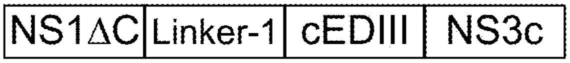
Figure 6C:
Figure 6D:
Figure 6E:
Figure 6F:
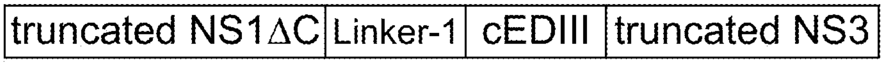
Figure 6G:
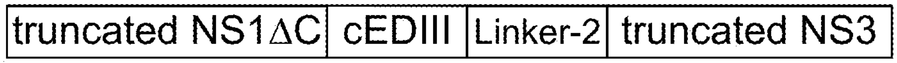
Figure 6H:
Figure 7A:
Figure 7B:
Figure 8A:
Figure 8B:
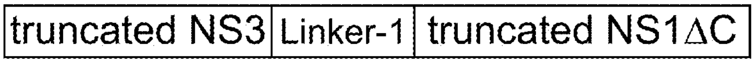
Figure 10A:
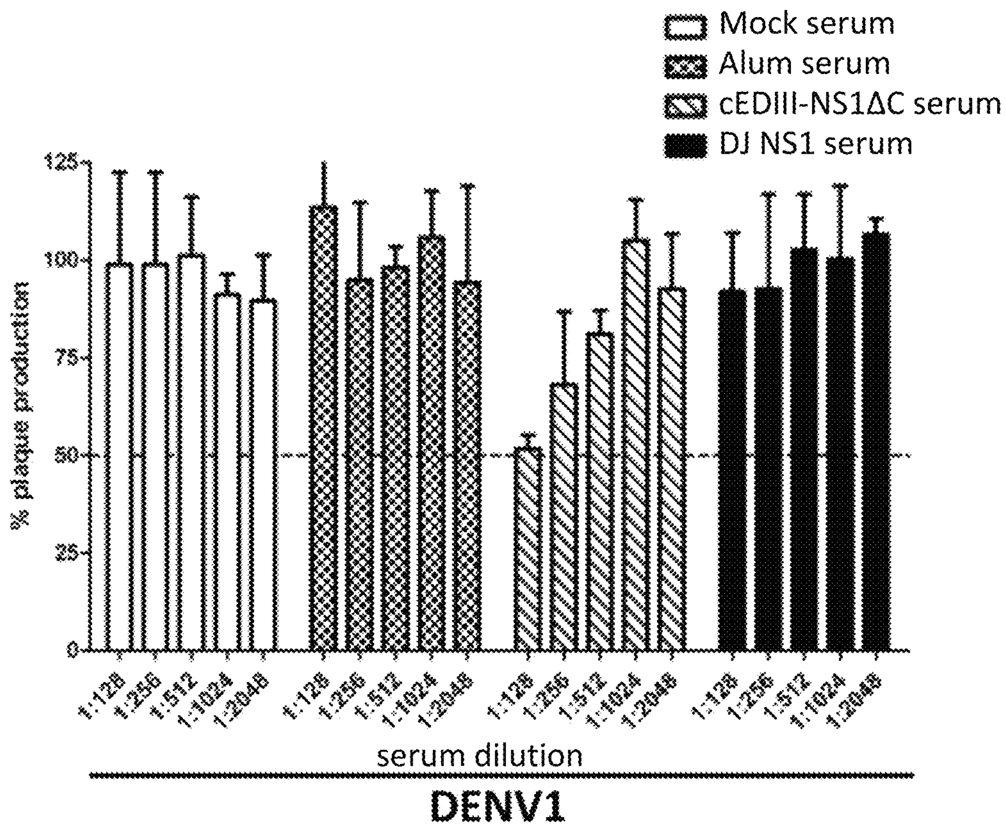
FIGS. 10A to 10D depict the results of determination of neutralizing antibody titers against four DENV serotypes in the serum of mice immunized with alum-mixed cEDIII-NS1ΔC or DJ NS1 protein. Two-fold serial dilutions of mock serum, alum serum, cEDIII-NS1ΔC serum and DJ NS1 serum were mixed with 50-80 PFU of DENV1 (FIG. 10A), DENV2 (FIG. 10B), DENV3 (FIG. 100) or DENV4 (FIG. 10D) for 1 h at room temperature and then inoculation into $1\times10^5$ BHK-21 cells. Neutralizing antibodies against DENV was determined by plaque reduction neutralization test (PRNT). Data from each group is expressed as the mean percentage of plaque production with SD bar (n=3).
Figure 10B:
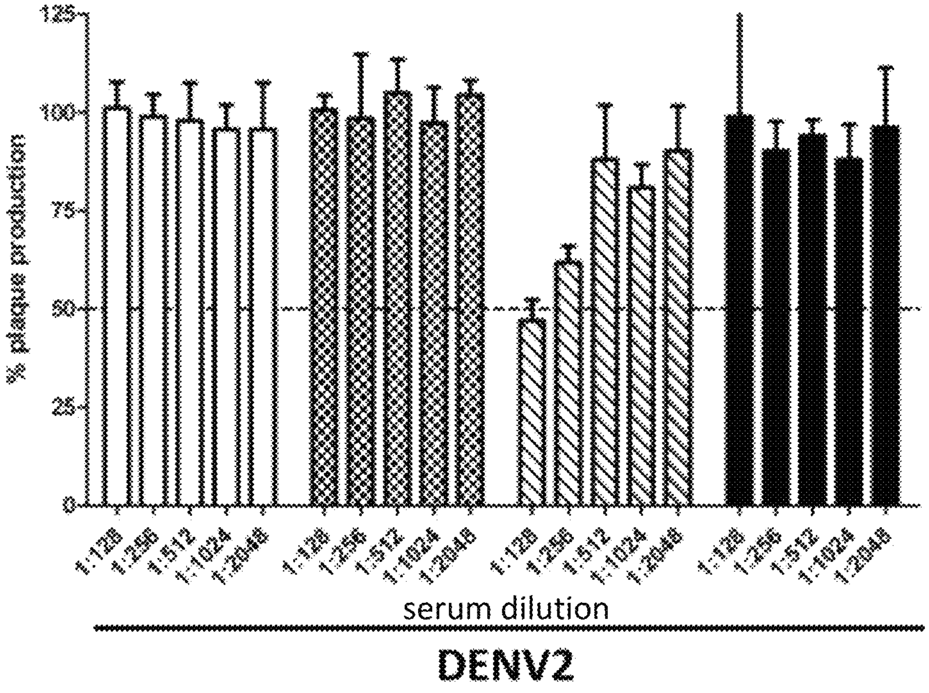
Figure 10C:
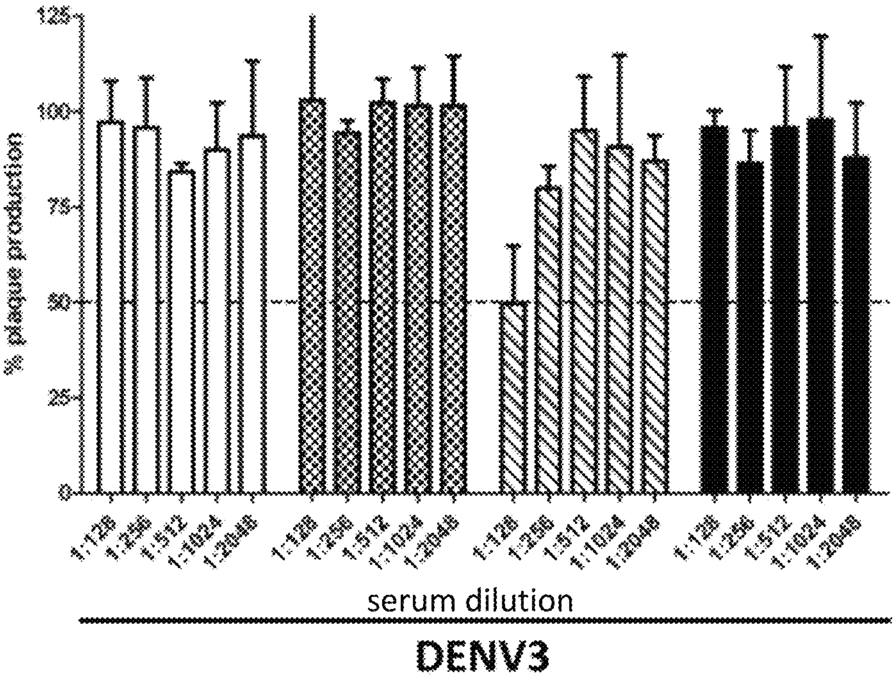
Figure 10D:
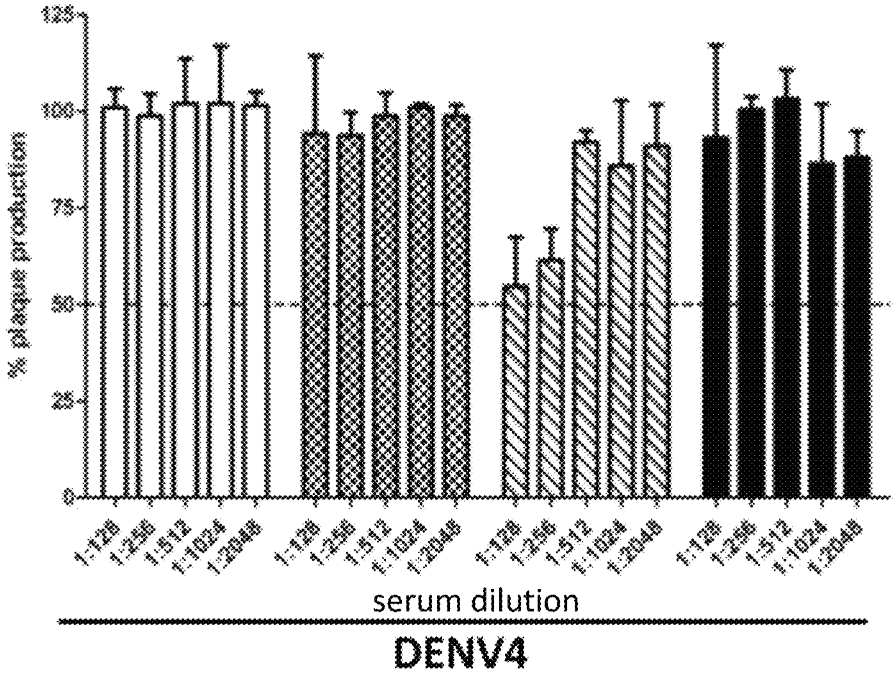
Figure 11A:
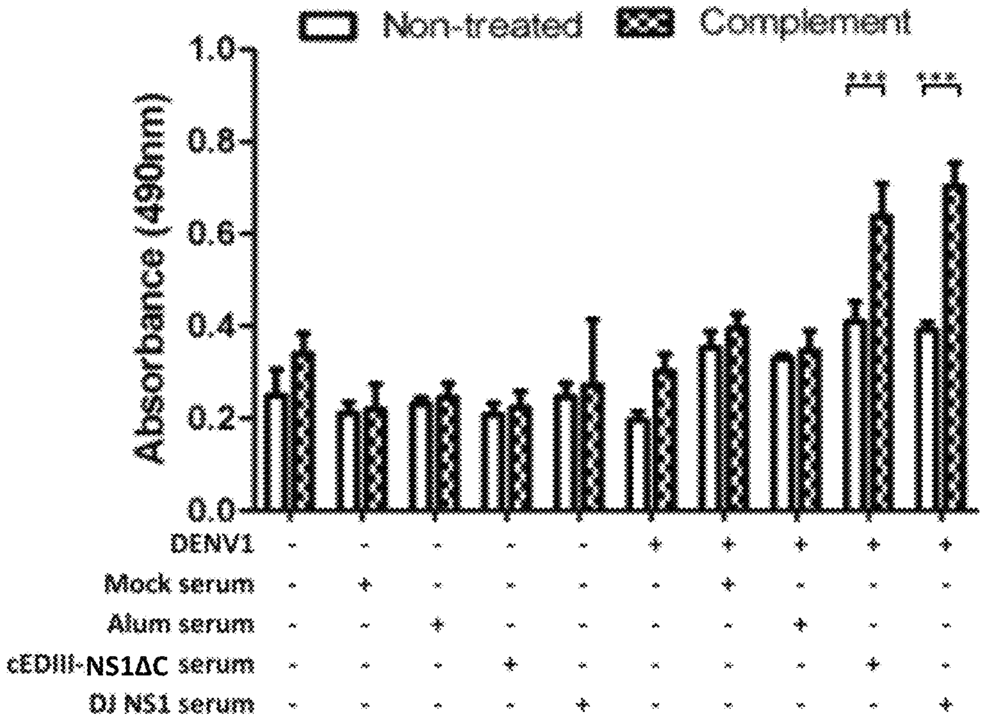
FIGS. 11A to 11D depict the results of serum of mice immunized with alum-mixed cEDIII-NS1ΔC or DJ NS1 protein causes complement-mediated cytolysis in cells infected by four different serotypes of DENV. HMEC-1 cells were individually infected with DENV1 (FIG. 11A), DENV2 (FIG. 11B), DENV3 (FIG. 11C) or DENV4 (FIG. 11D) (MOI=20) for 48 h. The cells then incubated with 1:200 dilution of mock serum, alum serum, cEDIII-NS1ΔC serum and DJ NS1 serum with or without complement for 6 h at 37° C. Cell supernatants were collected and assayed for the release of lactate dehydrogenase (LDH). The averages of triplicate cultures±SD are shown. : $p<0.01$; *: $p<0.001$ (n=3).
Figure 11B:
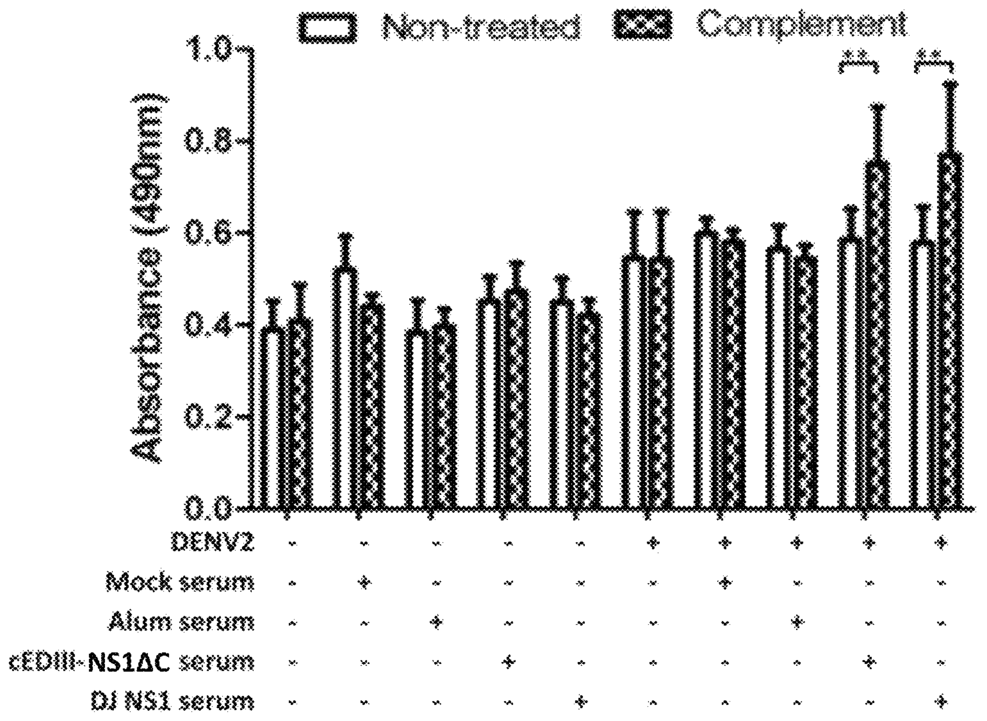
Figure 11C:
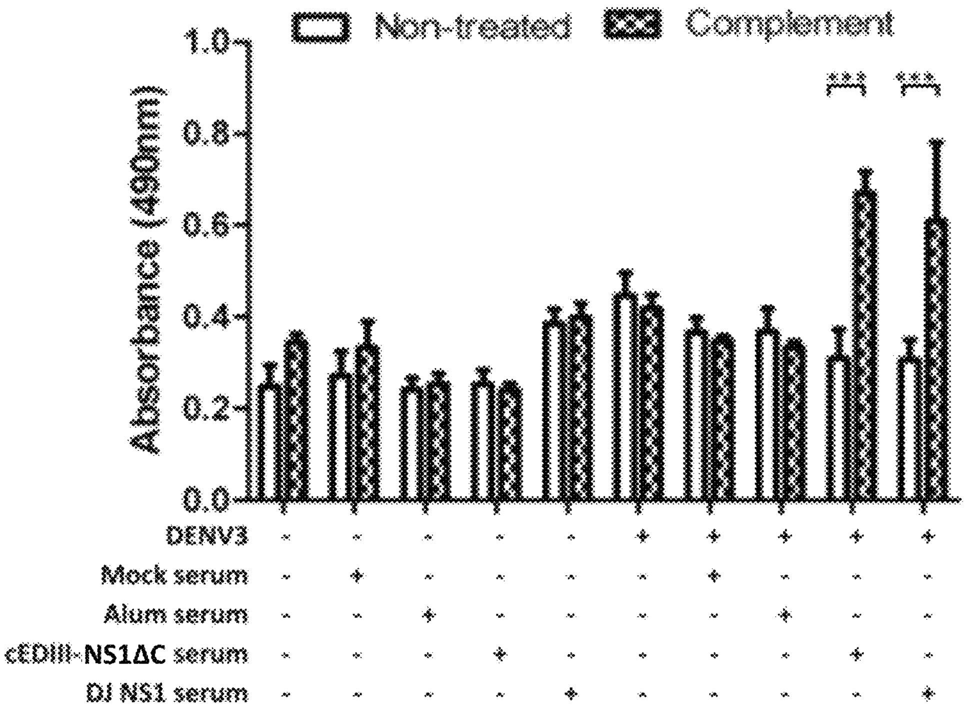
Figure 11D:
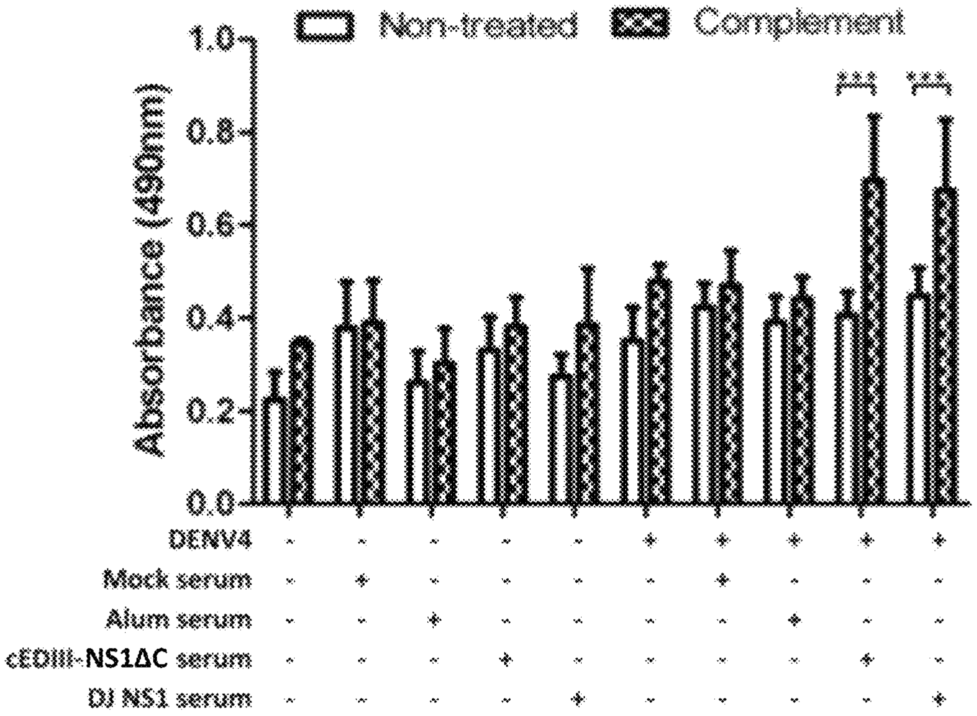
Figure 13A:
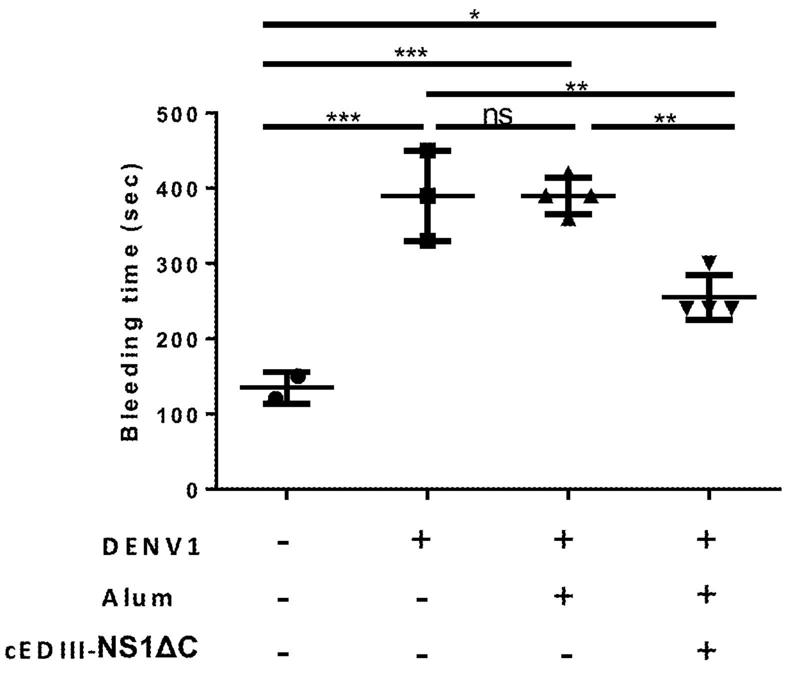
FIGS. 13A to 13D depict active immunization with cEDIII-NS1ΔC reduces DENV-induced prolonged bleeding time. Mouse model of immunization is shown in FIG. 12A. Mice were inoculated with $1\times10^8$ PFU of DENV1 (FIG. 13A), DENV2 (FIG. 13B), DENV3 (FIG. 13C), and DENV4 (FIG. 13D) by i.v. route at day 24. Mouse tail bleeding time was determined on 2 days post-infection. *p<0.05; p<0.01; *p<0.001; ****p<0.0001; ns: not significant.
Figure 13B:
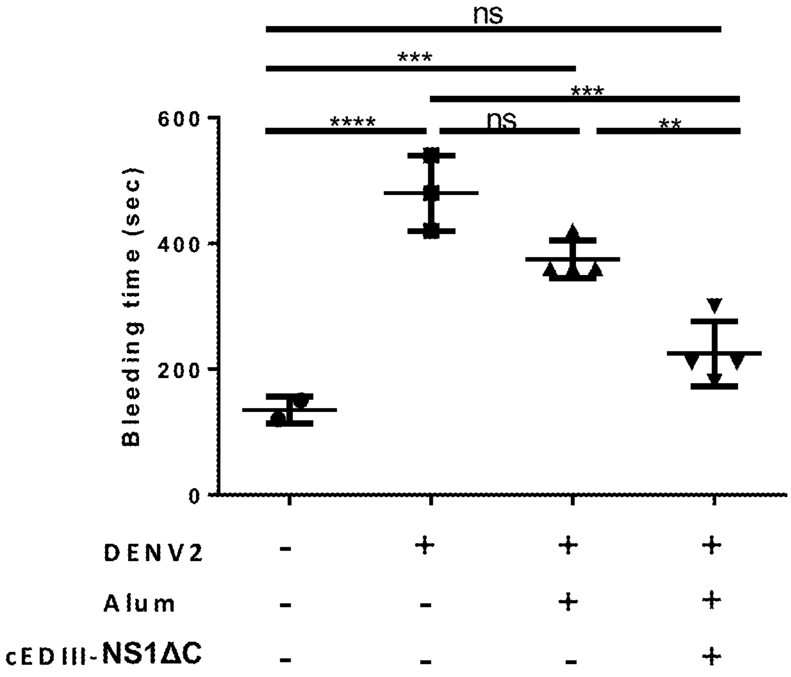
Figure 13C:
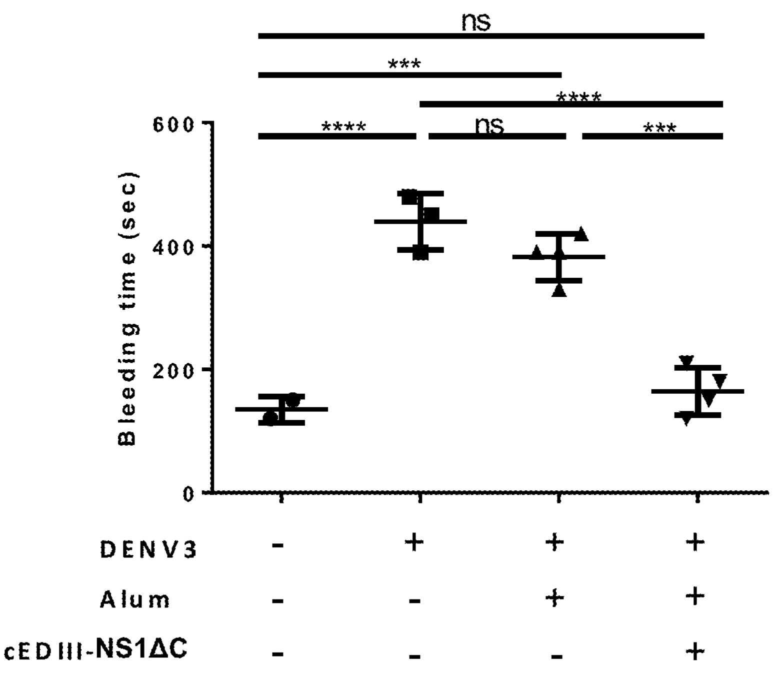
Figure 13D:
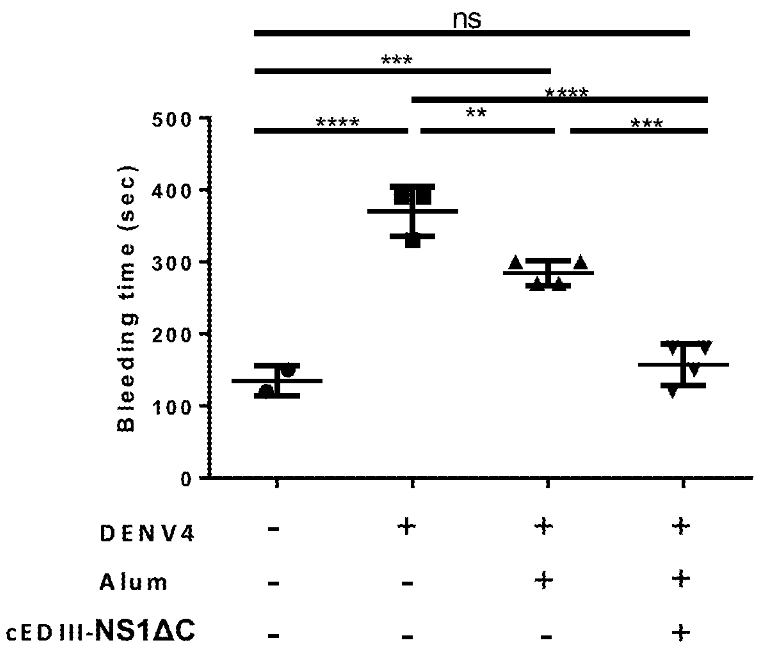
Figure 14A:
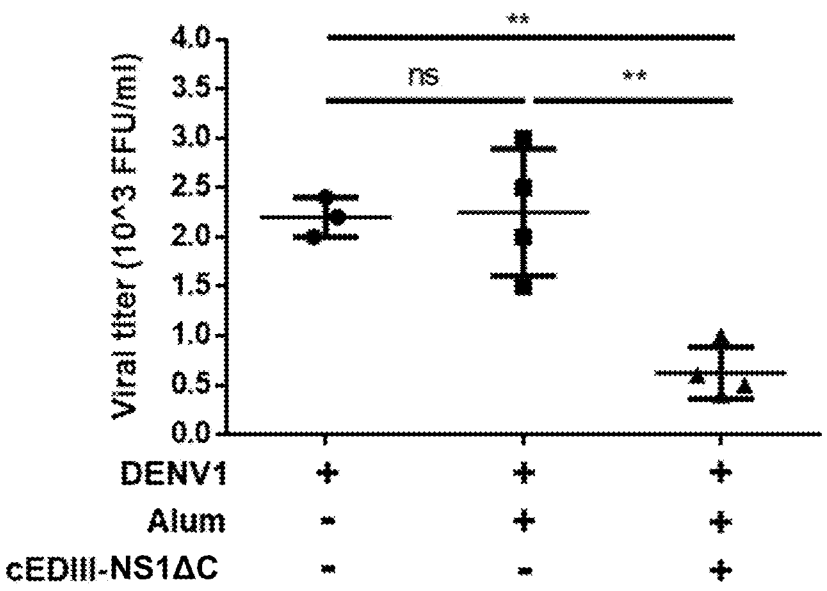
FIGS. 14A to 14D depict active immunization with cEDIII-NS1ΔC for reducing viral titers in mouse sera. Mice were inoculated with $1\times10^8$ PFU of DENV1 (FIG. 14A), DENV2 (FIG. 14B), DENV3 (FIG. 14C), and DENV4 (FIG. 14D) by i.v. route at day 24. Mice were sacrificed at 2 days post-infection. Sera were collected to detect the viral titers by fluorescent focus assay (FFA). p<0.01; *p<0.001; ****p<0.0001; ns: not significant.
Figure 14B:
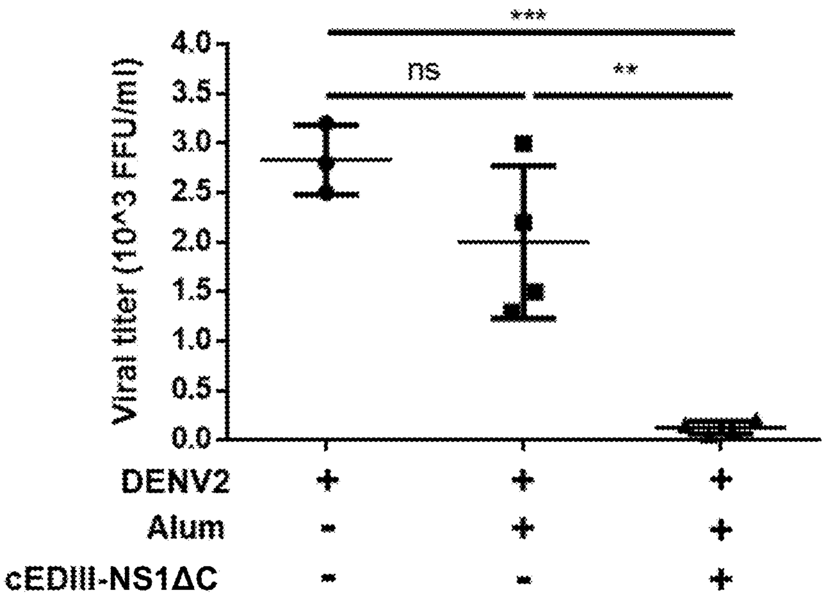
Figure 14C:
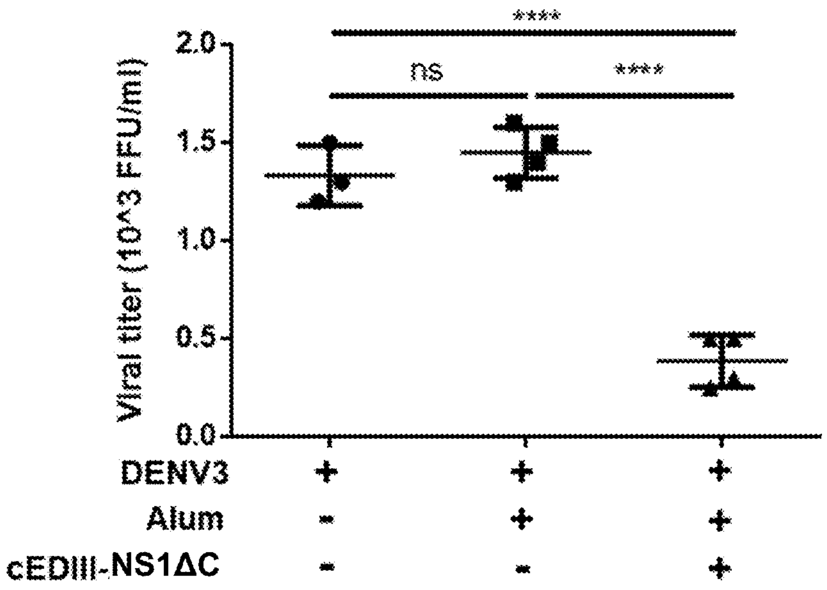
Figure 14D:
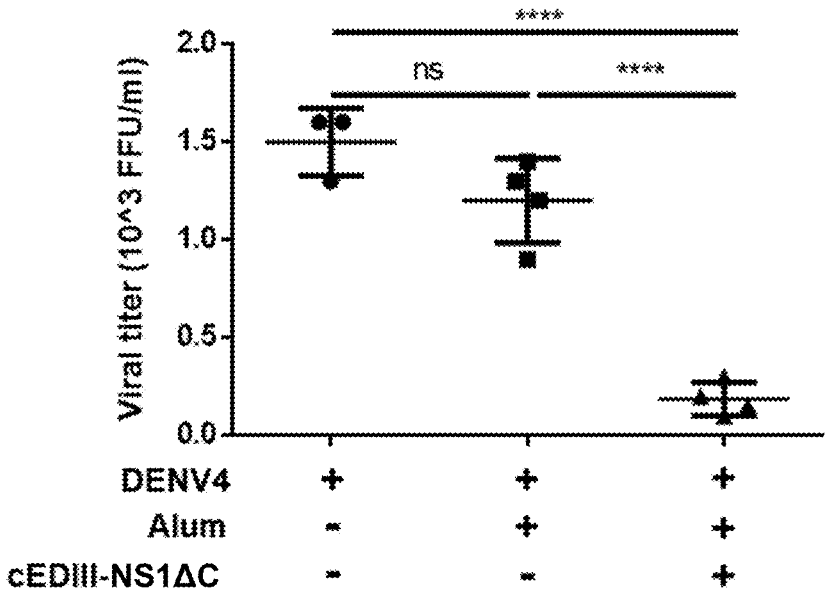

The embodiments of the invention will be apparent from the following detailed description, which proceeds with reference to the accompanying drawings, wherein the same references relate to the same elements.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

For purposes of interpreting this specification, the following definitions will apply and whenever appropriate, terms used in the singular will also include the plural and vice versa. Additional definitions are set forth throughout the detailed description.

The terms "a", "an", "the" and "said" as used herein are defined to mean "one or more" and include the plural unless the context is inappropriate.

The present invention discloses a composition of subunit dengue vaccine, which comprises a fusion protein of a delta C nonstructural protein 1 (NS1ΔC) polypeptide conjugating or connecting to at least one polypeptides of a NS3c polypeptide and/or a consensus envelope protein domain III (cEDIII), thereby enhancing better protection against DENV challenge and alleviating associated pathological effects. Moreover, the invention provides a composition of a subunit dengue vaccine comprising a NS3c polypeptide and a fusion protein of consensus envelope protein domain III and delta C nonstructural protein 1 (cEDIII-NS1ΔC). Alternatively, the invention provides a composition of a subunit dengue vaccine comprising a fusion protein of truncated NS1 polypeptide (or called as NS1fAC) and truncated NS3c polypeptide (or called as NS3cf). Alternatively, the composition also comprises polynucleotide segments encoding the aforementioned polypeptides.

The term "subunit dengue vaccine" recited herein includes a fusion protein of truncated dengue virus NS1 polypeptide conjugating or connecting to at least one polypeptides of a NS3c polypeptide and/or a cEDIII polypeptide, and when formulated together with a pharmaceutically acceptable carrier and an adjuvant, thereby enhancing better protection against DENV challenge and alleviating associated pathological effects.

In some embodiments, the term "fusion protein" recited herein refers to a NS1ΔC polypeptide (or truncated NS1ΔC) conjugating or connecting to at least one polypeptides of a NS3c polypeptide (or truncated NS3c) and/or a cEDIII polypeptide in any order, for example, cEDIII-NS1ΔC, NS1ΔC-cEDIII, NS1ΔC-NS3c, NS3c-NS1ΔC, cEDIII-NS1ΔC-NS3c, NS1ΔC-cEDIII-NS3c, NS3c-cEDIII-NS1ΔC, directly via a standard peptide-bond, i.e. with no additional linker, or via at least one additional linker such as linker-1 and linker-2, variants of the fusion proteins are shown in FIGS. 1A to 8B.

In certain examples, the "cEDIII" polypeptide can be exemplified as SEQ ID NOs:1 or 4. The "NS1ΔC" polypeptide can be exemplified as SEQ ID NOs:2 or 5. The "NS3c" polypeptide can be exemplified as SEQ ID NOs:3 or 6.

In other embodiments, the truncated NS1 polypeptide of the fusion protein can be listed as SEQ ID NO: 5, and the truncated NS3c polypeptide of the fusion protein can be listed as SEQ ID NO: 6. In these embodiments, the composition can optionally include a cEDIII polypeptide listed as SEQ ID NOs: 1 or 4. In certain embodiments, the fusion protein can optionally include a cEDIII polypeptide listed as SEQ ID NOs: 1 or 4, before, after or between the NS1ΔC and NS3c in any order.

In some embodiments, the linker such as linker-1 or linker-2 recited herein has to be indifferently understood as "linker" or "spacer", as commonly used in molecular biology. The linker can be any known oligopeptide or compound for conjugating or connecting NS1ΔC (or truncated NS1ΔC, NS1fAC) to at least one polypeptides of NS3c (or truncated NS3c, NS3cf) and cEDIII. In some examples, the linker can contain at least one amino acid, modified amino acid, or element that is a non-human amino acid. It may for instance contain one or several of the following elements: amino-3-oxapentanoic acid, PEG1, PEG2, PEG4, beta amino acid, gamma amino acid, aminohexanoic acid or amino-3,6-dioxaoctanoic acid.

The term "subunit dengue vaccine" can refer to the compositions as aforementioned, for enhancing better protection against DENV challenge and alleviating associated pathological effects.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

Certain exemplary embodiments according to the present disclosure are described as below, but these embodiments should not be considered as limiting the present invention. Various modification and changes can be made by one of ordinary skills in the art to which the present invention pertains, without departing from the spirit and scope of the present invention.

Examples

Establishment of Test Animal Model

C3H/HeN mice were obtained from Charles River Breeding Laboratories. They were maintained on standard laboratory food and water in the Laboratory Animal Center of National Cheng Kung University Medical College. Their 6-8-week-old or 3-week-old progeny were used for the generation of antibodies and infection experiments. The animal use protocol had been reviewed and approved by the Institutional Animal Care and Use Committee (IACUC). Embodiments hereinafter were approved by the Committee on the Ethics of Animals Experiments of National Cheng Kung University.

Preparation of Recombinant Proteins and Sera

The Example constructed the cEDIII-NS1ΔC by fusing the DNA fragment of NS1ΔC with the cEDIII construct (from Dr. Hsin-Wei Chen) using Not I and Xho I sites into pET21 b plasmid. As a result, the C-terminal end of the recombinant protein contains an additional hexahistidine tag (His-Tag). To express the protein, the construct was transformed into the *Escherichia coli* BL21 strains to generate *E. coli* that expressed cEDIII-NS1ΔC fusion protein. Bacteria were grown in Luria broth, induced with 0.5 mM isopropyl thiogalactoside (IPTG) and pelleted. Subsequently, bacteria were lysed after sonication. Because the cEDIII-NS1ΔC proteins were recovered as insoluble aggregate from the inclusion bodies, the cEDIII-NS1ΔC was denatured in the urea buffer (8 M urea, 500 mM NaCl, 20 mM Tris-HCl). The recombinant proteins were first purified by nickel ($Ni^{2+}$ column) and then refolded by slowly diluting out the denaturing reagents in the presence of L-arginine, EDTA, PMSF, reduced glutathione and oxidized glutathione. The Example concentrated it using Amicon Ultra-30 Centrifugal Filter Unit with Ultracel-30 membrane (Millipore). In addition, NS1ΔC (deletion of amino acids 271-352) and DJ NS1

(amino acids 1-270 of DENV NS1 and amino acids 271-352 of JEV NS1) cDNA were cloned into the pET28a vector with His-Tag. These plasmids were prepared by the Proteomic Research Core Facility, Academia Sinica. The cEDIII plasmid obtained from Dr. Hsin-Wei Chen was expressed in *E. coli* BL21. After purification, proteins were examined using 10% or 12% sodium dodecyl sulfate polyacrylamide gel electrophoresis (SDS-PAGE). The purified cEDIII-NS1ΔC was mixed with alum as adjuvant to immunize C3H/HeN mice subcutaneously for three times. Mouse sera were collected and antibody titers were determined seven days after first immunization, and three days after second and third immunization. After sacrifice, mouse sera were also collected and stored at −20° C.

DJ NS1 (aa 1-270 of DENV NS1 fused to aa 271-352 of JEV NS1) cDNA was cloned into pET28a vector with His-tag (Wan et al., 2014). The plasmid was prepared by the Proteomic Research Core Facility, Academia Sinica, Taiwan. Following introduction of the plasmids into *E. coli* BL21, the recombinant proteins were induced by 1 mM isopropyl B-D-1-thiogalaactopyranoside (IPTG) (Calbiochem, San Diego, CA), solubilized in urea buffer (8 M urea, 500 mM NaCl, and 20 mM Tris-HCl) and purified on a $Ni^{2+}$-NTA affinity column (GE Healthcare Life Science, UK). After purification, proteins were examined by SDS-PAGE, followed by staining with Coomassie brilliant blue R250. Purified proteins were dialyzed in refolding buffer (50 mM Tris-HCl, 250 mM NaCl, 1 mM EDTA, 250 mM L-arginine, 10 mM GSH [glutathione, reduced], and 1 mM GSSG [glutathione, oxidized], and 5% glycerol) and concentrated by Amicon Ultra Centrifugal Filters (Millipore, Billerica, MA).

DENV NS3 cDNA was cloned into pET21b vector with His-tag (provided from Dr. Chia-Yi Yu, National Health Research Institutes). The plasmids were used to transform *E. coli* BL21. Cells were grown overnight at 37° C. in Luria-Bertania (LB) medium containing 100 μg/ml of ampicillin. Overnight cultures were diluted 100-fold in the LB medium with 100 μg/ml of ampicillin and further incubated at 37° C. until the OD at 600 nm reached 0.5. DENV2 NS3 expression was then induced by the addition of 1 mM of IPTG for 6 h at 30° C. To analyze the expression of NS3 protein, samples were centrifuged at 8,000×g for 30 min at 4° C. Cells were harvested by centrifugation and the pellets were stored at −80° C. until use. The bacterial pellets were collected and analyzed by electrophoresis. For protein purification, pellets were resuspended in PBS and were lysed by sonication on ice. The cellular suspension was centrifuged at 13,000×g for 30 min. The pellet containing inclusion bodies was resuspended in binding buffer (8 M urea, 0.5 M NaCl, and 20 mM Tris-HCl, pH 6.95) and lysed by sonication on ice again and clarified by centrifugation at 13,000×g for 45 min at 4° C. The supernatant containing soluble protein was loaded onto a $Ni^{2+}$ column. The column was washed with washing buffer (8 M urea, 0.5 M NaCl, 20 mM Tris-HCl, and 120 mM imidazole, pH 6.95). His-tagged proteins were eluted with eluting buffer (8 M urea, 0.5 M NaCl, 20 mM Tris-HCl, and 300 mM imidazole, pH 6.95). After purification, proteins were examined by SDS-PAGE. Purified proteins were freed of urea by dialysis in refolding buffer (50 mM Tris-HCl, 250 mM NaCl, 1 mM EDTA, 250 mM L-arginine 10% glycerol, 10 mM GSH, and 1 mM GSSG, pH 6.95) and concentrated by Amicon Ultra for centrifugation (Millipore).

For mixing antigen with Alum, the Example first added Imject Alum (Pierce Biotechnology, Rockford, IL) dropwise with constant mixing to the antigen solution so the final volume ratio of Imject Alum to antigen was 1:1 (100 μl of Imject Alum to 100 μl of Ag). Then, continued mixing overnight at 4° C. to allow complete Imject Alum-antigen adsorption. Other clones were cloned by the aforementioned methods and their sequence identities were shown in Table 1.

TABLE 1

| | | Sequence identity (%) | | | | |
|---|---|---|---|---|---|---|
| | | DENV 1 | DENV 2 | DENV 3 | DENV 4 | ZIKV |
| Truncated NS1 (SEQ ID NO: 5) | DENV2 strain 16681 | 65-70 | — | 70-75 | 68-72 | 45-50 |
| Mimic cEDIII (SEQ ID NO: 4) | DENV2 strain 16681 | — | — | — | — | — |
| Truncated NS3 (SEQ ID NO: 6) | DENV3 strain D3/H/IMTSSA-SRI/2000/1266 | 90-95 | 93-96 | — | 90-92 | 80-85 |

Cell Cultures

Baby hamster kidney cells (BHK-21) were cultured in DMEM (Invitrogen, Carlsbad, CA) containing antibiotics and 5% FBS. C6/36 cells and L929 cells were cultured in DMEM containing antibiotics and 10% FBS. Lymphocytes were collected from mouse lymph nodes and cultured in RPMI-1640 medium containing antibiotics, 10% FBS, 1% nonessential amino acids, 1% sodium pyruvate, and 50 μM 2-ME at 37° C. in 5% $CO_2$. HMEC-1 cells were obtained from the Centers for Disease Control and Prevention, USA, and were passaged in culture flasks with endothelial cell growth medium M200 (Invitrogen) supplemented with 1 μg/ml hydrocortisone, 10 ng/ml epidermal growth factor, 3 ng/ml basic fibroblast growth factor, 10 μg/ml heparin, and antibiotics. Cells were detached using detaching buffer with 1000 U/ml trypsin and 0.5 mM EDTA.

Virus Culture

DENV2 strain 454009A was originally isolated from a dengue patient in Taiwan and maintained in C6/36 cells. Briefly, monolayers of C6/36 cells were incubated with DENV at a multiplicity of infection (MOI) of 0.01 and incubated at 28° C. in 5% $CO_2$ for 5 days. The cultured medium was harvested and cell debris was removed by centrifugation at 1000×g for 10 min. The virus supernatant was collected and stored at −70° C. until use. Virus titer was determined by plaque assay using BHK-21 cells. Briefly, BHK-21 cells were plated into 12-well plates ($8\times10^4$ cells/well) and cultured in DMEM under $CO_2$-enriched condition. After adsorption with serially diluted virus for 1 h, the inoculum was replaced with fresh DMEM containing 2% FBS and 0.8% methyl cellulose. Five days post-infection, the medium was removed, and the cells were fixed and stained with crystal violet solution consisting of 1% crystal violet, 0.64% NaCl, and 2% formalin.

Plaque Assay

BHK21 cells were seeded in 12-well ($1\times10^5$ cells/well) plates in DMEM with 5% FBS overnight at 37° C. under 5% $CO_2$ condition. Medium was then removed, serial dilutions of virus supernatants in DMEM with 2% FBS were added (0.4 ml/well), and the cells were incubated for 1 h at 37° C. Subsequently, DMEM containing 2% FBS and 0.8% methyl cellulose (Sigma-Aldrich; 1 ml/well) was added, and the plates were incubated at 37° C. for 5 days. Five days post-infection, the medium was removed, and the plaques were visualized after being fixed and stained with crystal violet solution (1% crystal violet, 0.64% NaCl, 2% formaldehyde) for 1.5 h at room temperature. Virus concentrations were determined as PFU/ml and used to calculate the multiplicity of infection (MOI) in infection experiments.

Plaque Reduction Neutralizing Test

Plaque reduction neutralization test (PRNT) was performed with the DENV1 strain 8700828, DENV2 strain 16681, DENV3 strain 8700829 and DENV4 strain 8700544 and different sera on BHK-21 cells in a manner analogous to that described above for plaque assay. Two-fold serial dilutions of sera (after 1 h complement-inactivated at 56° C.) were mixed with 50-80 PFU/well of DENV for 1 h at room temperature. Subsequently, virus-serum mixtures were added to BHK-21 cell monolayers for 1 h, and then the mixtures were replaced by DMEM containing 2% FBS and 0.8% methyl cellulose overlay. Five days later, the overlays were removed and the plaques were visualized after fixed and stained with the crystal violet solution (1% crystal violet, 0.64% NaCl, 2% formaldehyde) for 3 h at room temperature. At last, the concentration of serum to reduce the number of plaques by 50% compared to the serum-free virus designated as PRNT50 was graphed using Prism software.

Antibody Titer Determination

DJ NS1 or NS3 proteins were coated on 96-well plates at 0.2 μg/well in coating buffer ($Na_2CO_3$ 1.59 g, $NaHCO_3$2.93 g, pH 9.6, in 1 L $ddH_2O$) at 4° C. overnight. The plates were blocked with 5% BSA in PBS at 4° C. overnight, and then washed three times with 0.05% Tween 20 in PBS. Mouse sera were diluted serially and the diluted mouse sera were added to protein-coated wells, and incubated at 4° C. overnight. After washing three times, HRP-conjugated anti-mouse IgG (Cell Signaling, Danvers, MA) or IgM (KPL, Gaithersburg, MD) was added into each well and incubated for 2 h at room temperature. After washing, ABTS was added into each well and the absorbance was measured by microplate reader at 405 nm (Emax microplate reader, Molecular Devices, Sunnyvale, CA).

Analysis for Dendritic Cell and $CD4^+$ and $CD8^+$ T Cell Activation

In the ex vivo studies, pooled lymph node cells were double-stained or triple-stained with PE-conjugated anti-CD11c (eBioscience, San Diego, CA), combined with APC-conjugated anti-CD40 or CD86 (BioLegend, San Diego, CA), PE-Cy7-conjugated anti-CD80 (BioLegend), and FITC-conjugated MHC class I or II antibodies (BioLegend) to determine dendritic cell activation. Cells were analyzed by flow cytometry (CytoFLEXs, Beckman Coulter, Brea, CA).

Pooled lymph node cells ($5\times10^5$ cells/ml) were cultured in 24-well plates and stimulated with DJ NS1 or NS3 (5 μg/ml) for 3 days. Cells were harvested and triple-stained with PE-conjugated anti-CD25 (eBioscience), FITC-conjugated anti-CD4, and PE-Cy7-conjugated anti-CD8 antibodies (BD Biosciences, San Jose, CA) to determine T cell activation. Cells were analyzed by flow cytometry (CytoFLEXs).

Analysis for Surface CD107a of $CD8^+$ T Cells

Pooled lymph node cells ($5\times10^5$ cells/ml) were cultured in 24-well plates and stimulated with DJ NS1 or NS3 (5 μg/ml) for 3 days. At day 3, cells were further stimulated with anti-CD3/CD28 (0.5 μg/ml) (eBioscience), and PerCP/cy5.5-conjugated CD107a antibodies (BioLegend) were added to the cells prior to stimulation. The cultures were incubated for 4 h at 37° C. in 5% $CO_2$ in the presence of the secretion inhibitor, Brefeldin (BioLegend), and monensin (BD Biosciences) to inhibit cytotoxic granule acidification and receptor-mediated endocytosis retaining CD107a on cell surface. Cells were harvested and triple-stained with PE-Cy7-conjugated anti-CD8 antibodies (BD Biosciences) to determine T cell degranulation. Cells were analyzed by flow cytometry (CytoFLEXs).

Intracellular Staining of NS3 Expression in L929 Cells

NS3-expressing L929 cells ($5\times10^5$ cells/ml) were washed with PBS and fixed with 4% paraformaldehyde in PBS at room temperature for 10 min. After washing with PBS, cells were permeabilized with permeabilized buffer (0.5 g saponin, 5 g BSA and 0.5 g $NaN_3$ in 500 ml PBS) and stained with anti-NS3 antibody overnight at 4° C. After washing with permeabilized buffer, cells were incubated with Alexa-488-conjugated anti-mouse IgG (Invitrogen, Carlsbad, CA) for 1 h at room temperature. After a final two washes with PBS, cells were analyzed by flow cytometry (CytoFLEXs).

Active Immunization and DENV Infection Mouse Model

Three-week-old mice were immunized s.c. with 25 μg/mouse of DJ NS1 protein with alum, 12.5 μg/mouse of NS3 protein with alum, 25 μg DJ NS1 protein plus 12.5 μg NS3/mouse with alum, alum alone, and PBS control at days 0 and 14. Mouse sera and lymph node cells were collected at day 21 for assays. For the DENV infection model, mice were challenged i.v. with DENV2 ($1\times10^8$ PFU/mouse) at day 17, and sacrificed and the plasma and tissues were collected at day 19.

Viral Titers Analysis

To determine the viral titers in mouse sera, fluorescent focus assay (FFA) was performed. In brief, sera was serially diluted with RPMI medium with 2% FBS and incubated with BHK-21 cells at 37° C. for 2 h. Then, the monolayer was replaced with DMEM containing 2% FBS and 0.8% methylcellulose and incubated at 37° C. After 2-3 days, the overlays were removed and virus foci were stained with anti-NS1 antibody (mAb 33D2, obtained from Dr. Trai-Ming Yeh). Alexa 488-conjugated goat anti-mouse IgG (Invitrogen) was added and visualized with a fluorescence microscope.

NS1 Quantitative ELISA

To quantify the concentration of NS1 in the blood of mice, homemade NS1 sandwich ELISA was performed. In brief, 5 μg/ml anti-NS1 mAb 33D2 was coated onto 96-well plates at 4° C. overnight. After blocking for 1 h with 1% BSA in PBS, mouse sera (1:5 dilution) were co-incubated with 1 μg/ml biotin-conjugated anti-NS1 mAb 31B2 (obtained from Dr. Trai-Ming Yeh) on wells at 37° C. for 1-2 h. HRP-labeled streptavidin solution (1:40) (R&D Systems, Minneapolis, MN) was added into wells at 37° C. for 20 min. After washing with PBST (PBS contained 0.01% Tween 20) 3 times, color development and visualization with tetramethylbenzidine (TMB) was performed. The absorbance was read following the addition of stop solution (2 N $H_2SO_4$) by microplate reader at OD 450 nm (Emax microplate reader, Molecular Devices).

Bleeding Time

The bleeding time was determined before euthanasia at two days after DENV infection. To measure mouse-tail bleeding time, a 3-mm tail-tip was transacted. Bleeding time was performed with a 3-mm tail-tip transection. Blood droplets were collected on filter paper every 30 sec. Bleeding time was recorded when the blood spot was smaller than 0.1 mm in diameter.

Enzyme-Linked Immunosorbent Assay (ELISA)

ELISA plates were coated with 100 μl of the recombinant proteins (cEDIII, NS1ΔC, DJ NS1 or cEDIII-NS1ΔC) diluted in coating buffer at a concentration of 2 μg/ml. The plates were incubated at 4° C. overnight. The plates were incubated with 200 μl of 5% BSA/coating buffer for 2 h at room temperature, and then washed three times with 200 μl of PBST (0.05% tween 20 in PBS). Two-fold serially diluted antiserum (100 μl) was added and incubated at 37° C. for 2 h or at 4° C. overnight. The plates were washed three times with 200 μl of PBST. The HRP-conjugated secondary antibody (100 μl, 1:5000 in PBS) was added and incubated at 37° C. for 2 h. After washing with 200 μl of PBST for three times, the reaction was visualized with the addition of ABTS (100 μl). After sufficient color development, the absorbance was detected by ELISA reader at 415 nm.

Antibody-Dependent Complement-Mediated Cytolytic Assay

HMEC-1 cells were seeded into 96-well plates ($5\times10^3$ cells/well) then incubated overnight at 37° C. in 5% $CO_2$ in a 37° C. incubator. After discarding the supernatant, HMEC-1 cells were incubated with DENV (MOI=20) in M200 medium for 48 h. After washing with PBS twice, cells were incubated with 1:200 dilution of mock serum, alum serum, cEDIII-NS1ΔC serum or DJ NS1 serum prepared in phenol-red-free M200 medium and then with or without Low-Tox-M rabbit complement (1:20 dilution) for 6 h at 37° C. in 5% $CO_2$ to facilitate complement-mediated cell lysis. Cytolysis was measured by the release of lactate dehydrogenase (LDH), a cytoplasmic enzyme, with a commercial kit (Cytotoxicity detection kit). The optical density was determined by a microplate reader at 490 nm.

Immunization and DENV-Infection Mouse Model

C3H/HeN mice were subcutaneously immunized with alum-mixed recombinant cEDIII-NS1ΔC. Mouse sera were collected and antibody titers were determined seven days after first immunization, and three days after second and third immunization. Four days after the third immunization, DENV2 was intradermally inoculated in C3H/HeN mice on the upper back. Mouse tail bleeding time was determined and mice were sacrificed at 3 days post-infection, and mouse sera were also collected and store at −20° C.

Expression of Recombinant NS1fΔC-cEDIII-NS3cf and NS1fΔC-NS3cf Proteins Using Mammalian 293F and *Drosophila* S2 Cells Expression Systems Two recombinant proteins (NS1fΔC-cEDIII-NS3cf and NS1fΔC-NS3cf with molecular weights of 49 and 35 kDa, respectively) were cloned into pTT5 vector with His-tag in both ends of protein. The plasmids were transfected into 293F cells, and the recombinant proteins were secreted by 293F cells into supernatant. The supernatants with recombinant proteins were collected 5 days after transfection and were purified with $Ni^{2+}$ column. After purification, recombinant proteins were frozen-dried and stored at −20° C. Recombinant protein from 293F cells used in our experiment were designed and provided by Leadgene Biomedical, Inc. Additionally, in order to produce recombinant proteins in a more stable and better purification condition, proteins were cloned into pMT/BiPA/5 vector with His-tag and Strep-tag in two ends and the plasmids were transfected into *drosophila* S2 cells. Recombinant protein-expressing stable clone of *drosophila* S2 cells was established by Dr. Yen-Chung Lai. Cells were first cultured in standing 75T flask with 20 ml Schneicher's *Drosophila* medium at room temperature (RT) and were shaken at 65 rpm. 1000 ml plastic Erlenmeyer flask was used to culture cells after cells grew to the concentration of 1.5 to $2\times10^7$ cells/ml in four 75T flask. Cells were then cultured and shaken at 80 rpm for 3 days until grew to 3 to $5\times10^6$ cells/ml in 500 ml medium in plastic Erlenmeyer flask. Recombinant proteins were induced by the addition of 500 mM copper sulfate in 500 μl for 3 days at RT. To analyze the expression of recombinant proteins, samples were centrifuged at 1500 rpm for 10 min at RT to collect supernatant. Collected 500 ml supernatant was then mixed with 50 ml binding buffer (50 mM $NaH_2PO_4$, 300 mM NaCl, pH 8.0) and passed through a cup filter. The recombinant protein-containing supernatant was loaded through column with Strep-tactin sepharose. The column was washed with washing buffer (50 mM $NaH_2PO_4$, 300 mM NaCl, pH 8.0). Recombinant proteins with Strep-tag were eluted with eluting buffer (50 mM $NaH_2PO_4$, 300 mM NaCl, 2.5 mM desthiobiotin, pH 8.0). After purification, proteins were examined using 12% SDS-PAGE and Western blot, and were dialyzed overnight using 10K dialysis membrane into PBS base. The dialyzed proteins were then quantified by Bradford protein assay and frozen-dried by Leadgene Biomedical, Inc.

Focus Reduction Neutralization Test (FRNT)

BHK-21 cells were seeded into 96-well plates ($1\times10^4$ cells/well) and cultured in 37° C. incubator for 12 to 16 h until the cell confluency reached 60-70%. Sera from immunized mice were 10-fold diluted in DMEM medium with 2% FBS, and 50 μl of virus medium containing 50-100 plaques was added into the diluted sera at RT for 1 h. Subsequently, the medium from 96-well μlate was removed, 100 μl of the serum-virus mixture was added into BHK-21-containing wells and incubated in 37° o incubator for 1-1.5 h. Then, 100 μl of methyl cellulose medium was added directly into wells and incubated for 2-2.5 days. Cells were fixed by 4% paraformaldehyde for 1 h at 37° C., and then the primary antibody (anti-NS1 mAb 33D2 plus anti-DENV serotypes 1-4 antibodies in 0.5% Triton X-100 solution) was added into wells and stained overnight at 4° C. Virus foci were stained by FITC-conjugated goat anti-mouse IgG and visualized by fluorescence microscopy.

Statistical Analysis

Data were expressed as the means±SD. All data were analyzed using Prism software (GraphPad, San Diego, CA). Bleeding time and viral titers were analyzed by one-way ANOVA. Compliment-dependent cytolysis assay was analyzed by two-way ANOVA. Statistical significance was set at $p<0.05$.

Results

Immunization with the Recombinant cEDIII-NS1ΔC Protein Induces Antibody Responses Specific to cEDIII and NS1ΔC Protein The diagram of proteins used in this embodiment including cEDIII, NS1ΔC, DJ NS1 and a linear fusion of cEDIII-NS1ΔC recombinant proteins is shown (FIG. 9A). C3H/HeN mice at 6 to 8-week-old were subcutaneously immunized with cEDIII-NS1ΔC, DJ NS1 or DJ NS1 plus cEDIII mixed in alum as adjuvant (FIG. 9B). After mice were sacrificed, antibody titers were determined. The example coated cEDIII, DJ NS1 and NS1ΔC proteins separately on 96-well plate and added mouse serum as primary antibodies then analyzed by ELISA. The antibody titers after 2nd dose and 3rd dose of immunization were determined (FIG. 9C).

The cEDIII-NS1ΔC-Immunized Mouse Serum Neutralizes all Four DENV Serotypes

The mouse sera induced by cEDIII-NS1ΔC protein contain anti-NS1ΔC and anti-cEDIII antibodies. Because the anti-E antibodies play a role in neutralizing DENV, it was evaluated whether the cEDIII-NS1ΔC-immunized mouse serum could neutralize all four DENV serotypes in this example. To validate the neutralization capacity of immunized mouse serum, the example conducted a plaque reduction neutralization test. Two-fold serum dilution of mock serum, alum serum, cEDIII-NS1ΔC serum and DJ NS1 serum were mixed with DENV1, DENV2, DENV3 or DENV4 and then added to BHK-21 cells which were seeded on a 12-well μlate. Only the group of cEDIII-NS1ΔC-immunized mouse serum neutralized DENV1, DENV2, DENV3 and DENV4 in a dose-dependent manner and showed a 50% reduction in plaque count at a dilution of 1:128. However, DJ NS1-immunized mouse serum could not neutralize any of DENV serotypes (FIGS. 10A to 10D).

The cEDIII-NS1ΔC-Immunized Mouse Serum Destroys Cells Infected by all Four DENV Serotypes Through Antibody-Complement-Mediated Cytolysis NS1 is dimerized after posttranslational modification in the lumen of the ER and is expressed on the surface of infected cells. Previous studies of the inventors showed that anti-NS1ΔC antibodies could provide protection by complement-mediated cytotoxicity in vitro. Hence, the example wondered whether the cEDIII-NS1ΔC serum containing anti-NS1ΔC antibodies could cause complement-mediated cytolysis on all four DENV serotypes. Thus, the example conducted an antibody-dependent complement-mediated cytolytic assay. HMEC-1 cells seeded in 96-well plates were infected by DENV1, DENV2, DENV3 or DENV4. Then, cells were incubated with 1:200 dilution of mock serum, alum serum, cEDIII-NS1ΔC serum or DJ NS1 serum with or without complement. Cytolysis was measured by the release of LDH. Both cEDIII-NS1ΔC- and DJ NS1-immunized mouse serum mixed with complement caused cytolysis on cells infected by four different serotypes of DENV as compared to other groups (FIGS. 11A to 11D). Because NS1ΔC was generated from NS1 of DENV2, these finding showed the cross-protection of DENV2 NS1ΔC to all DENV serotypes.

Immunization with cEDIII-NS1ΔC Protein Reduces DENV-Induced Prolonged Bleeding Time in Mice C3H/HeN mice were subcutaneously (s.c.) immunized with alum-mixed recombinant cEDIII-NS1ΔC protein for three times (FIG. 12A). The serum antibody titers against cEDIII and DJ NS1 were determined (FIG. 12B). Then, it was tested the protective effect of cEDIII-NS1ΔC protein of which mice were intravenously (i.v.) inoculated with different serotypes of DENV. Results showed that the cEDIII-NS1ΔC-immunized mice displayed lower mouse-tail bleeding time induced by four different serotypes of DENV as compared with mice infected with DENV alone or DENV plus alum (FIGS. 13A-13D).

Immunization with cEDIII-NS1ΔC Protein Reduces DENV Titer in Mouse Serum

To check for the effect of cEDIII-NS1ΔC immunization on viral replication, the viral titer in mouse serum were determined. Results showed that lower viral titers (FIGS. 14A-14D) were detected in mouse sera after cEDIII-NS1ΔC immunization when mice were infected by different DENV serotypes as compared with mice infected with DENV alone or DENV plus alum.

Immunization with DJ NS1 and NS3 Induces Dendritic Cell and Specific $CD4^+$ and $CD8^+$ T Cell Activation in Response to DJ NS1 or NS3 Antigen Ex Vivo To evaluate the dendritic cell (DC) activation after immunization, the example analyzed the expression of CD40, CD80, CD86, MHC I and MHC II in $CD11c^+$ lymph node dendritic cells (LNDCs). The results showed that most $CD11c^+$ LNDCs express MHC class I, and mice immunized with 25 μg DJ NS1 and 12.5 μg NS3 induced LNDCs exhibited significantly higher MHC class I than other groups including alum alone, DJ NS1 alone, and NS3 alone. The MHC II expression of $CD11c^+$ LNDCs was increased in mice immunized with DJ NS1 alone or NS3 alone; and although not statistically significant, there was a trend of increase in mice immunized with combination of DJ NS1 plus NS3. Active immunization with DJ NS1 alone, NS3 alone, or DJ NS1 plus NS3 in mice induced a trend of increase of CD40 expression in $CD11c^+$ LNDCs although with no statistical significance. Active immunization with DJ NS1 alone, NS3 alone, or combination of DJ NS1 plus NS3 all significantly increased CD80 expression on $CD11c^+$ LNDCs as compared with PBS control at day 21. Only the combination of DJ NS1 plus NS3 significantly increased CD86 expression on $CD11c^+$ LNDCs as compared with alum alone and the PBS control group. Thus, these results indicate that active immunization with DJ NS1 plus NS3 can induce DC activation as measured by increased DCs that express co-stimulatory receptors (data not shown).

Figure 15A:
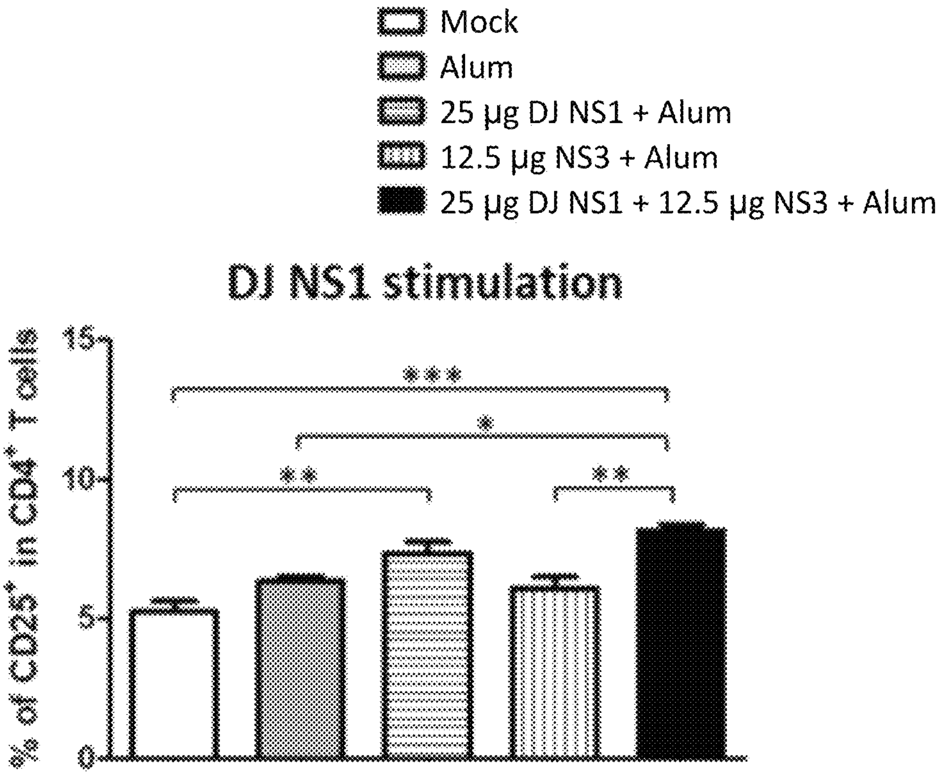
FIGS. 15A to 15D depict the results of active immunization levels (%) with DJ NS1 and NS3 induces both $CD4^+$ and $CD8^+$ T cell activation in response to DJ NS1 or NS3 antigen stimulation ex vivo. C3H/HeN mice were immunized s.c. with different doses of immunogen, i.e. 25 μg DJ NS1 plus 12.5 μg NS3/mouse, 25 μg DJ NS1/mouse, 12.5 μg NS3/mouse, alum alone or PBS at day 0 and boosted at day 14. Mice were sacrificed at day 21 and lymph node (LN) cells were collected and re-stimulated with 5 μg/ml DJ NS1 or NS3 proteins for 3 days and incubated with anti-CD3/CD28 antibodies for the final 4 h, then triple-stained with PE-labeled anti-CD25, FITC-labeled anti-CD4, and PE/Cy7-labeled anti-CD8 to analyze the CD25 expression of $CD4^+$ and $CD8^+$ T cells by flow cytometry.
Figure 15B:
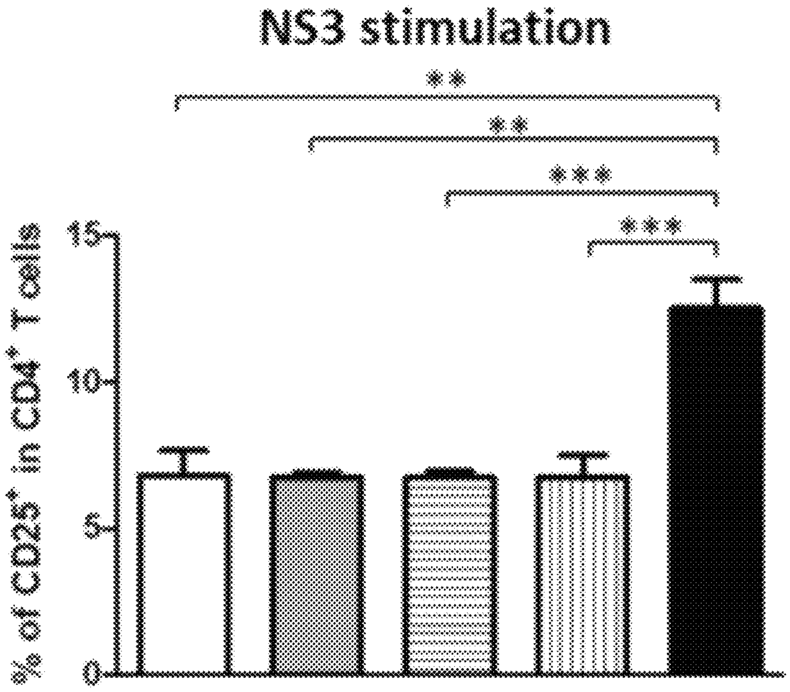

To evaluate whether DJ NS1 and NS3 can induce antigen-specific T cell responses, lymph node cells were collected from immunized mice and re-stimulated with 5 μg/ml DJ NS1 or NS3 proteins for 3 days. Anti-CD3 and anti-CD28 antibodies were administered to all groups to partially mimic TCR signals and amplify responses. Active immunization of mice with DJ NS1 alone or DJ NS1 plus NS3 significantly induced $CD4^+$ T cell activation in response to DJ NS1 antigen stimulation compared to alum alone or PBS control (FIG. 15A). Only active immunization with DJ NS1 plus NS3 in mice significantly induced $CD4^+$ T cell activation in response to NS3 antigen stimulation compared to other groups (FIG. 15B). Active immunization with DJ NS1 plus NS3 also significantly induced $CD8^+$ T cell activation in response to DJ NS1 antigen stimulation (FIG. 15C) as well as to NS3 antigen stimulation (FIG. 15D) compared to other groups. Therefore, active immunization with DJ NS1 plus NS3 can induce both $CD4^+$ and $CD8^+$ T cell activation in response to DJ NS1 or NS3 antigen stimulation.

Active Immunization with DJ NS1 and NS3 Induces Specific CTL Responses

Figure 15C:
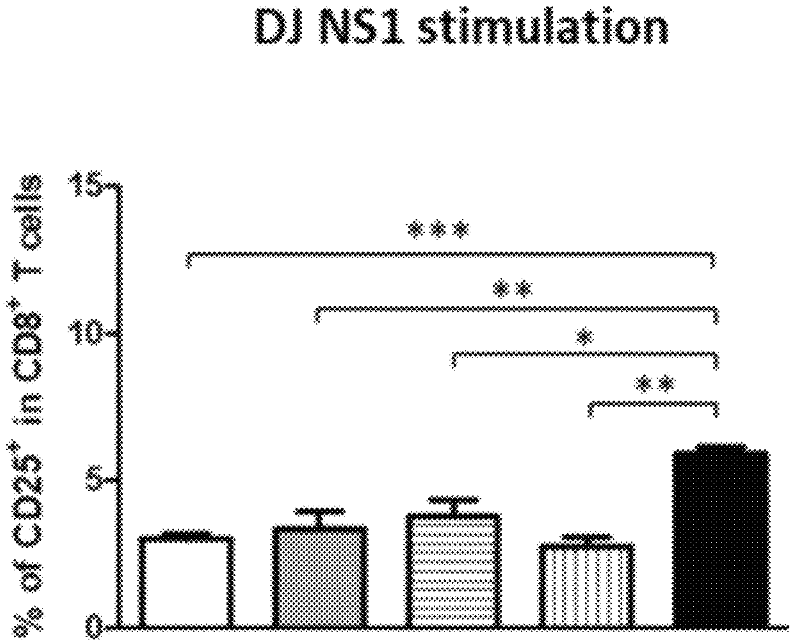
Figure 15D:
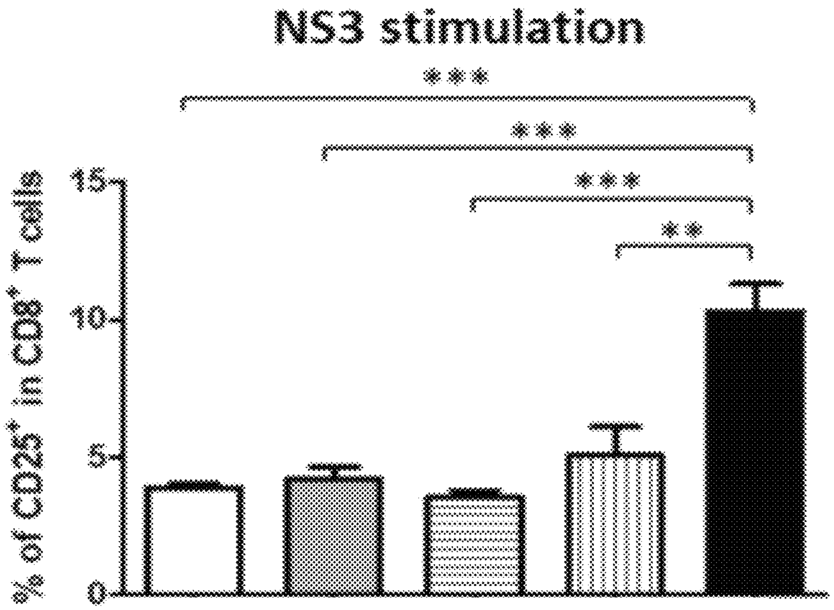
Figure 16A:
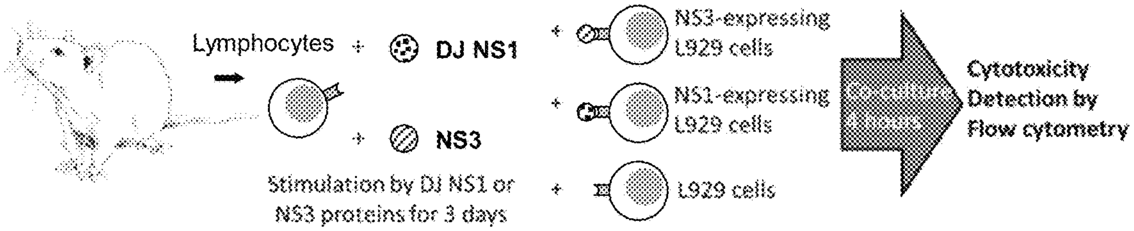
FIGS. 16A to 16C depict the results of active immunization with DJ NS1 and NS3 induces cytotoxic T lymphocyte (CTL) responses against NS3-expressing L929 cells.
Figure 16B:
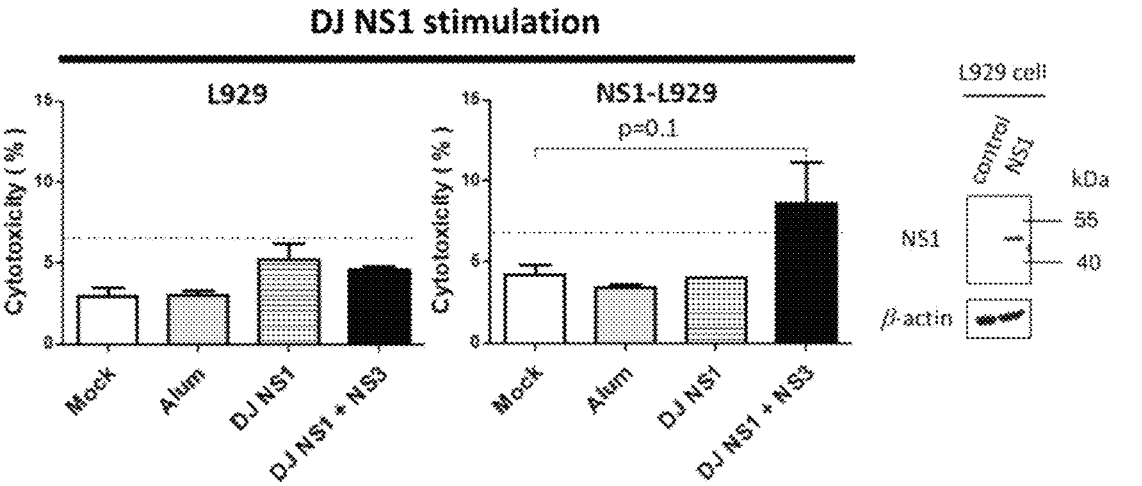
Figure 16C:
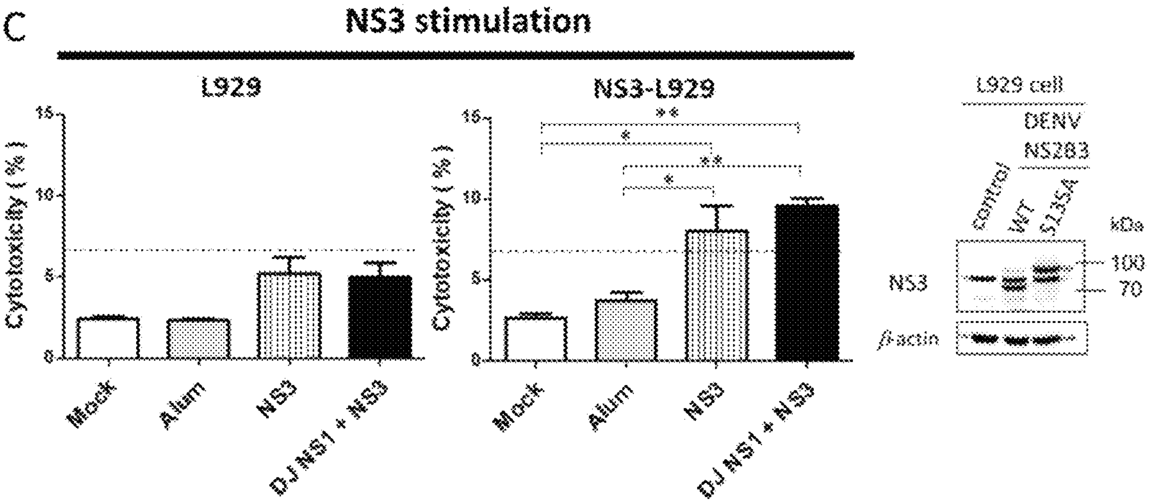

Previous studies showed that $CD8^+$ T cells could directly contribute to protection against DENV. In the study of the inventors, active immunization with DJ NS1 plus NS3 induced $CD8^+$ T cell activation (FIGS. 15C to 15D). To examine whether a CTL response can be induced, the example isolated lymph node cells from immunized mice and re-stimulated with DJ NS1 or NS3 protein and then cocultured with DJ NS1-expressing or NS3-expressing L929 cells as the target for 4 h (FIG. 16A). To generate NS3-expressing L929 cells, the example established L929 cells expressing either a wild type NS2B3 or a proteolytically inactive mutated version, NS2B3-S135A (Rodriguez-Madoz et al., 2015). NS2B3-S135A-expressing L929 cells were then used as target cells due to better expression levels (data not shown). Results showed that only CTLs from DJ NS1 plus NS3 immunized mice lysed NS1-expressing L929 cells, however, with no statistical difference compared to other groups (FIG. 16B). On the other hand, CTLs from NS3 alone or DJ NS1 plus NS3 immunized mice significantly lysed NS3-expressing L929 cells (FIG. 16C).

Figure 17A:
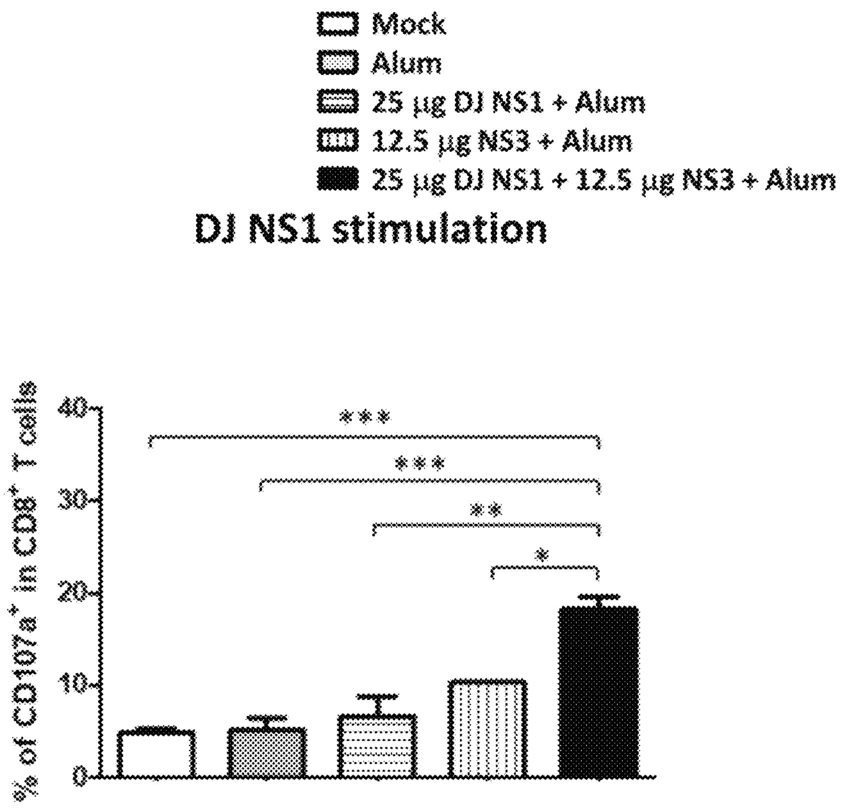
FIGS. 17A to 17B depict the results of increased expression of CD107a, a marker for cytotoxic $CD8^+$ T cell activity, in the DJ NS1 and NS3-immunized mice after DJ NS1 (FIG. 17A) or NS3 (FIG. 17B) antigen stimulation ex vivo. Mice were sacrificed at day 21 and lymph node cells were collected and re-stimulated with 5 μg/ml DJ NS1 or NS3 proteins for 3 days, and then incubated with anti-CD3/CD28 antibodies, monensin, and brefeldin A for the final 4 h to perform surface staining of CD107a expression in $CD8^+$ T cells by flow cytometry. n=5 for DJ NS1 plus□NS3 group and n=4 for other groups. The averages of each group±SD are shown. *p<0.05, p<0.01, *p<0.001, as determined by one-way ANOVA with Tukey post hoc test.
Figure 17B:
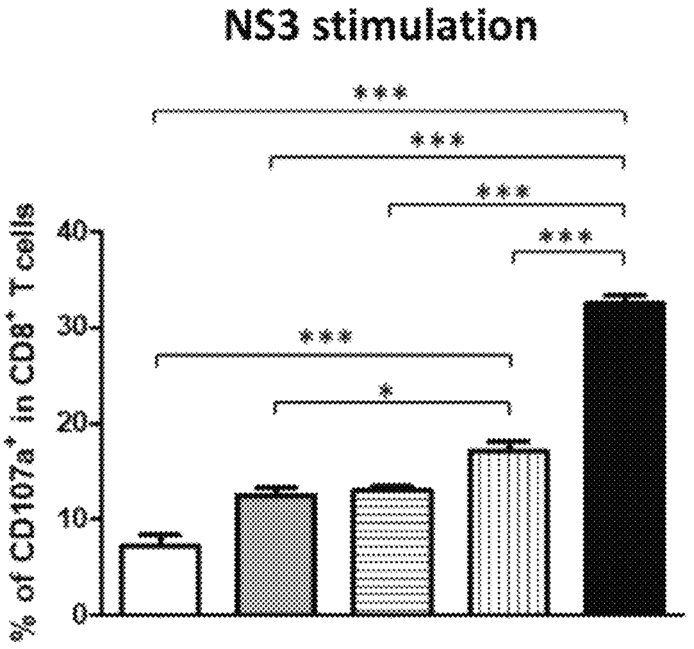

In addition to demonstrating CTL activity on target cells, the example further determined the cytotoxic activity of effector cells directly. The lipid bilayer of cytotoxic granule in $CD8^+$ T cells contains lysosomal-associated membrane glycoproteins (LAMPs), including CD107a (LAMP-1); therefore, CTL degranulation leads to cumulative exposure of CD107a on the cell surface. Based on the fact that degranulation of activated $CD8^+$ T cells occurs rapidly after TCR stimulation, lymph node cells isolated from immunized mice were re-stimulated with DJ NS1 or NS3 protein for three days and incubated with anti-CD3 and anti-CD28 to partially mimic TCR signals during the last 4 h. Active immunization with DJ NS1 plus NS3 significantly increased CD107a expression on the surface of $CD8^+$ T cells in response to both DJ NS1 (FIG. 17A) and NS3 (FIG. 17B) stimulation compared to NS3 alone, DJ NS1 alone, alum alone, and PBS control. The CD107a expression on the surface of $CD8^+$ T cells from NS3-immunized mice was also significantly increased in response to NS3 stimulation compared to alum alone and PBS control, but was less than that from DJ NS1 plus NS3-immunized mice (FIG. 17B). Results from FIGS. 16A to 17B indicate that active immunization with DJ NS1 plus NS3 can induce antigen-specific CTL responses.

Figure 18A:
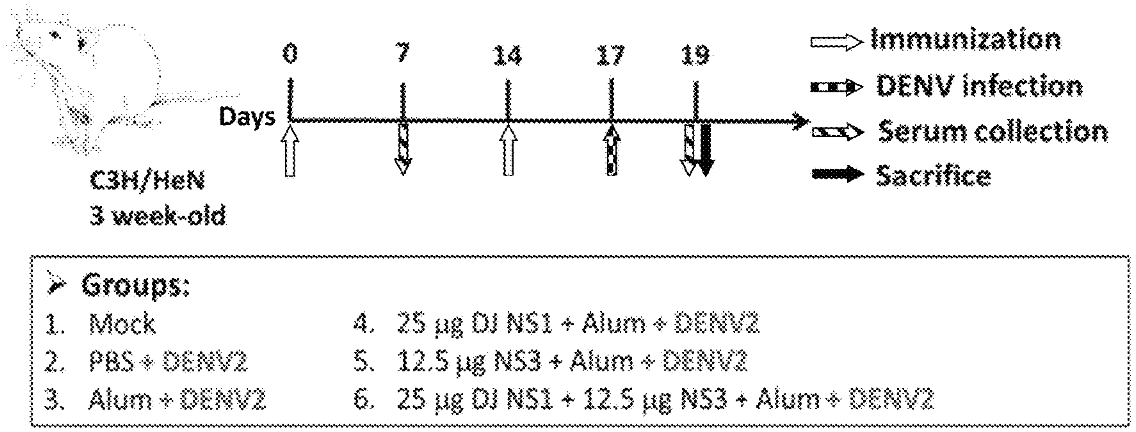
FIGS. 18A to 18C depict the results of active immunization with DJ NS1 and NS3 for reducing viral titers in the serum of DENV-infected mice.

Active Immunization with DJ NS1 and NS3 Provides Protective Effects Against DENV Infection The example next established a DENV infection model to evaluate the protection provided by active immunization with DJ NS1 plus NS3 as shown in FIG. 18A.

Figure 18B:
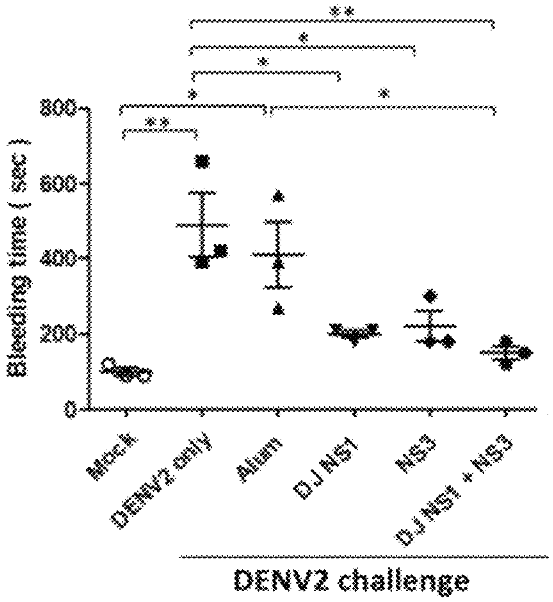

Our previous studies demonstrated that mice inoculated with high titer DENV can produce pathogenic signs such as prolonged bleeding time and local hemorrhaging (Wan et al., 2014). Accordingly, the example evaluated the protection provided by active immunization with DJ NS1 and NS3 by determining the DENV-induced prolonged bleeding time. The results showed that DENV infection caused prolonged bleeding time in mice 48 h post DENV infection alone or with alum. Active immunization with DJ NS1, NS3, or DJ NS1 plus NS3 significantly reduced DENV-induced prolonged bleeding time compared to DENV infection alone (FIG. 18B).

Figure 18C:
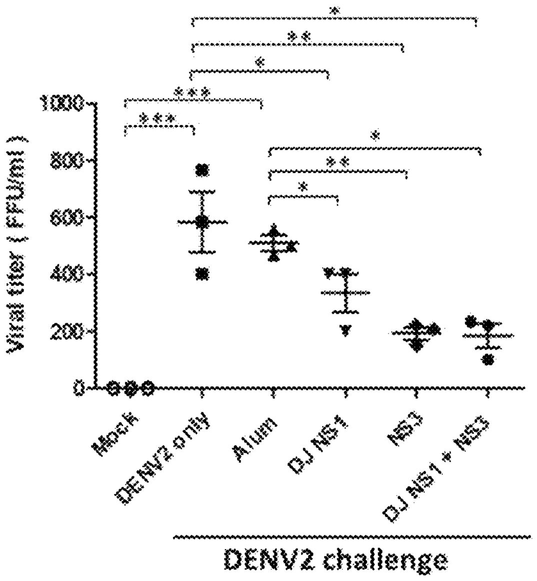

The example determined the viral titers at day 19. DJ NS1 protein can induce antibody responses that trigger antibody-dependent complement-mediated cytolysis of DENV-infected cells (Wan et al., 2017). In agreement with previous findings of the inventors, active immunization with DJ NS1 alone significantly reduced viral titers compared to the DENV2 only and alum control (FIG. 18C). Active immunization with NS3 alone more significantly reduced viral titers than with DJ NS1 alone. The NS3-specific T cell responses shown in the present study may thus contribute to viral clearance. The reduced viral titers after active immunization with DJ NS1 plus NS3 were comparable to those after immunization with NS3 alone.

These results indicate that active immunization with DJ NS1 or DJ NS1 plus NS3 provide better protective effects against vascular leakage.

Discussion

Active Immunization with DJ NS1 and NS3 Provides Protective Effects Against DENV Infection According to the aforementioned embodiments, the recombinant protein, cEDIII-NS1ΔC, can be used as a subunit vaccine candidate for antiviral strategy. As a non-replicating protein-based subunit vaccine, it would be considered as a safer option.

Due to the concern of a conformational change of recombinant cEDIII-NS1ΔC that might affect the immune efficacy, the combination of cEDIII and DJ NS1 proteins were used for comparison with fusion protein. In those embodiments, immunization with a combination of cEDIII (5 μg) and DJ NS1 (20 μg) to mice could elicit optimal antibody titers specific for cEDIII and DJ NS1 proteins, which showed similar antibody titers as the group immunized with 25 μg cEDIII-NS1ΔC (data not shown). cEDIII-NS1ΔC chosen as following vaccine strategy.

EDIII has a low potential for inducing cross-reactive antibodies to heterologous DENV serotypes, which has been implicated in the pathogenesis of severe illness (Chin et al., 2007). Mice immunized with recombinant DENV EDIII proteins which were designed by four strains of viruses produced serotype-specific IgG1 neutralizing antibodies that exhibited measurable enhancing activity in FcγR-bearing cells to DENV. An engineered DENV2-based resurfaced EDIIIs (rsDIIIs) protein showed decreased binding to antibodies targeting unfavorable epitopes but maintaining high affinity to those broadly DENV neutralizing antibodies. A cEDIII, which contains a consensus sequence from EDIII of four DENV serotypes would also be considered as a potential vaccine candidate. It has been reported that antibodies from mice with the immunization of cEDIII showed neutralizing capacity to all serotypes of DENV. Individual monkeys immunized with cEDIII also showed elevated neutralizing antibodies in sera (Chen et al., 2013; Leng et al., 2009). In this study, recombinant protein cEDIII-NS1ΔC not only induced neutralizing antibodies from C3H/HeN mice against four serotypes of DENV in vitro but also provided a protective efficacy for mice against DENV infection in vivo. It was observed that mice had lower viral titers and soluble NS1 in sera of those immunized with cEDIII-NS1ΔC after DENV infection when compared with DENV only group.

The pathogenic effect of DENV NS1 has been emphasized in previous studies with various mechanisms. Therefore, NS1 has been proposed as a good target against the pathogenesis caused by DENV. NS1-induced endothelial hyperpermeability can be reversed by anti-NS1 mAb treatment (Chen et al., 2016). NS1 vaccination can also prevent the endothelial permeability and vascular leak triggered by DENV NS1 (Beatty et al., 2015). Previous studies identified the major cross-reactive epitopes in C-terminal region of DENV NS1 (Cheng et al., 2009). Therefore, the NS1 protein with C-terminal deletion was considered as a safer subunit vaccine candidate to avoid autoimmunity. The previous study of the inventors showed that antibodies specific for NS1ΔC possessed the ability of antibody-mediated complement-dependent cytotoxicity (Wan et al., 2014). Mice immunized with cEDIII-NS1ΔC not only induced antibodies that can destroy four serotypes of DENV-infected cells but reduced the prolonged bleeding time induced by DENV in mice.

Although the exact role of T cells during DENV infection and disease is still a matter of debate, many evidence supports a protective role for T cells in DENV infection currently in both human and mouse studies (Katzelnick et al., 2017; Kao 2019). Nonstructural protein has been reported to contain many T cell activation epitopes. NS1 was also mentioned possessing a critical role for protection against DENV in the activation of $CD4^+$ and $CD8^+$ T cells. Therefore, the specific T cell response of cEDIII-NS1ΔC protein can be further studied in the future. Combined NS1ΔC and NS3 was tested as a vaccine strategy against DENV infection (Kao et al., 2019). In the future, cEDIII-NS1ΔC plus NS3 protein will be a candidate for vaccine development. Due to Dengvaxia® contains prM and E genes but without nonstructural proteins of DENV, no antibody specific to dengue NS1 protein nor effective nonstructural proteins-specific T cell response will be produced. In these embodiments, cEDIII contains a consensus sequence from EDIII of four DENV serotypes and NS1ΔC was generated from NS1 of DENV2, those results showed the cross-protective activity of cEDIII-NS1ΔC protein to all four DENV serotypes.

Based on the aforementioned results, cEDIII-NS1ΔC protein induces high antibody response specific to envelope protein and NS1 protein with neutralizing and complement-dependent cytolysis function against DENV and the DENV-infected cells, respectively. In the mouse protection model, pretreatment with cEDIII-NS1ΔC protein also induced high antibody titers specific to envelope protein and NS1 protein in mice. Moreover, cEDIII-NS1ΔC-immunized group reduces DENV-induced prolonged bleeding time and viral titer in mouse sera after infection by four different DENV serotypes. Therefore, cEDIII-NS1ΔC protein is a potential vaccine candidate to provide protection against DENV infection. Dengue is an important mosquito-borne viral disease of humans globally in terms of morbidity and economic impact (Bhatt et al., 2013). Despite the global dengue burden, there are no specific dengue therapeutics or safe and effective vaccines, and prevention is currently limited to vector control measures. There are still several obstacles for the development of dengue vaccines and antiviral drugs. One is that the complicated pathogenesis is still not fully resolved. Another obstacle is the lack of appropriate animal models (Coller et al., 2011; Wan et al., 2013). Recently, several groups have generated tetravalent live-attenuated vaccines but the safeness and protective efficacy remain to be proved. In these embodiments, the example generated a fusion protein, cEDIII-NS1ΔC as a subunit vaccine for antiviral strategy. Immunization with recombinant cEDIII-NS1ΔC protein produced antibodies which have capacity to neutralize DENV and destroy DENV-infected cells. Immunization with cEDIII-NS1ΔC protein also reduced DENV-induced bleeding tendency and soluble NS1 concentration in mouse plasma. The possible mode or actions of cEDIII-NS1ΔC-elicited antibodies may involve neutralization capability and antibody-mediated complement-dependent cytolysis.

Several type- and subtype-specific neutralizing antibodies have been mapped to EDIII (Gromowski et al., 2007; Wahala et al., 2009; Guzman et al., 2010), and anti-EDIII antibodies are recognized as the most powerful blockers of virus infectivity (Gromowski et al., 2007). Anti-EDIII antibodies are present in primary and secondary DENV immune human sera. However, anti-EDIII antibodies constituted only a small proportion of the total antibody in immune sera binding to DENV (Wahala et al., 2009). It is thought that EDIII is responsible for receptor binding (Kuhn et al., 2002; Klein et al., 2013). The EDIII is exposed and accessible on the virion surface and recombinant EDIII proteins inhibit virus infectivity (Chin et al., 2007; Guzman et al., 2010; Coller et al., 2011). Importantly, EDIII has a low potential for inducing cross-reactive antibodies to heterologous DENV serotypes, which has been implicated in the pathogenesis of severe illness (Chin et al., 2007; Guzman et al., 2010).

There are many recombinant subunit vaccine candidates which are based on EDIII in preclinical development. The International Centre for Genetic Engineering and Biotechnology in India developed a tetravalent chimeric EDIII fusion protein expressed in *Pichia pastoris*. The tetravalent chimeric EDIII protein consists of the EDIII domains of DENV1, 2, 3, and 4 joined by flexible peptide linkers. Immunization of mice with the tetravalent vaccine candidate adjuvanted with montanide resulted in neutralizing antibody responses against all DENV serotypes. Production of tetravalent dengue vaccines must be cost-effective for vaccines to be affordable in resource-poor areas of the world. In order to make a single multivalent component, the cEDIII which contains a consensus sequence from EDIII of four DENV serotypes would be a good vaccine candidate (Leng et al., 2009; Chen et al., 2013). Mice immunized with the recombinant cEDIII developed neutralizing antibodies against all serotypes of DENV.

Another group of antibodies elicited by immunizing with cEDIII-NS1ΔC protein is anti-NS1ΔC antibodies. The present inventors had identified major cross-reactive epitopes in the C-terminus of DENV NS1 (Cheng et al., 2009; Chen et al., 2009, Wan et al., 2008). Therefore, the NS1 protein with a C-terminal deletion would be a safer subunit vaccine candidate to prevent autoimmunity. Moreover, previous study of the inventors demonstrated that anti-NS1ΔC antibodies possessed the ability of antibody-mediated complement-dependent cytotoxicity (Wan et al., 2014). In this embodiment, the cEDIII-NS1ΔC-immunized mouse serum caused cytolysis in HMEC-1 cells infected by four different serotypes of DENV. In addition to antibody-mediated complement-dependent cytotoxicity, other mechanisms by which anti-NS1ΔC antibodies contribute to protection from DENV challenge need to be further determined, such as protection from NS1-induced vascular permeability.

The ideal vaccines or antiviral drugs must be protective against each of the four DENV serotypes without the risk of ADE (Wan et al., 2013). Non-neutralizing or sub-neutralizing antibodies against DENV E and PrM cross-reactive across the four DENV serotypes may enhance viral entry and infection. DENV NS1 is not a virus surface structure protein, so antibodies against NS1 will not cause ADE. In this embodiment, the example verified that cEDIII-NS1ΔC serum neutralized all four DENV serotypes and destroyed DENV-infected HMEC-1 cells through antibody-mediated complement-dependent cytolysis. To verify the protective effect of cEDIII-NS1ΔC protein, immunization with cEDIII-NS1ΔC protein mixed with alum provided the protective effect by reducing the prolonged bleeding time induced by DENV2 infection.

Dengvaxia® contains only prM and E genes of DENV, but no DENV NS proteins, therefore cannot produce antibody specific to NS1 protein and have no effective NS protein-specific T-cell response. In contrast, the cEDIII-NS1ΔC protein not only produces neutralizing antibodies but also produces antibody specific to NS1 protein, resulting in more comprehensive protection against DENV infection. The specific T-cell response of cEDIII-NS1ΔC protein may be further studied. In addition to this, the immunization of Dengvaxia® was reported with adverse effects. The cEDIII-NS1ΔC protein is a DENV protein subunit vaccine but not a full viral particle, therefore, the probability of causing serious side-effects is much lower than other live-attenuated vaccines.

The price of dengue vaccines should be affordable to the individuals who most need the vaccines in resource-poor areas of the world. In this embodiment, the cEDIII protein fused with NS1ΔC protein saving the cost and speed-up protein purification. Moreover, DENV NS3-induced $CD8^+$ T cell responses were shown to be protective against heterotypic DENV re-infection, thus reduce the risk of ADE. Therefore, it is worthwhile to test cEDIII-NS1ΔC plus NS3 protein as candidate for vaccine development. Due to a lack of glycosylation of the subunit vaccine expressed in *E. coli*, the example had expressed the recombinant proteins in mammalian cells and *drosophila* cells.

The results of FIGS. 9A to 18C were summarized in Table 2. The cEDIII-NS1ΔC fusion protein could provide better immunoprotective effect than the mixtures of the recombinant proteins DJ NS1 and NS3 regarding to inhibition of viral titer, reduction of sNS1 level and reduction of prolonged bleeding time.

TABLE 2

| Immunogen group | | cEDIII-NS1ΔC (25 μg) | DJ NS1 (25 μg) + NS3 (12.5 μg) |
|---|---|---|---|
| | Protection | | |
| Viral control in serum | Inhibition of viral titer | **** | * |
| | Reduction of sNS1 level | ** | *** |
| Animal Protection | Reduction of prolonged bleeding time | * | ** |

Figure 19:
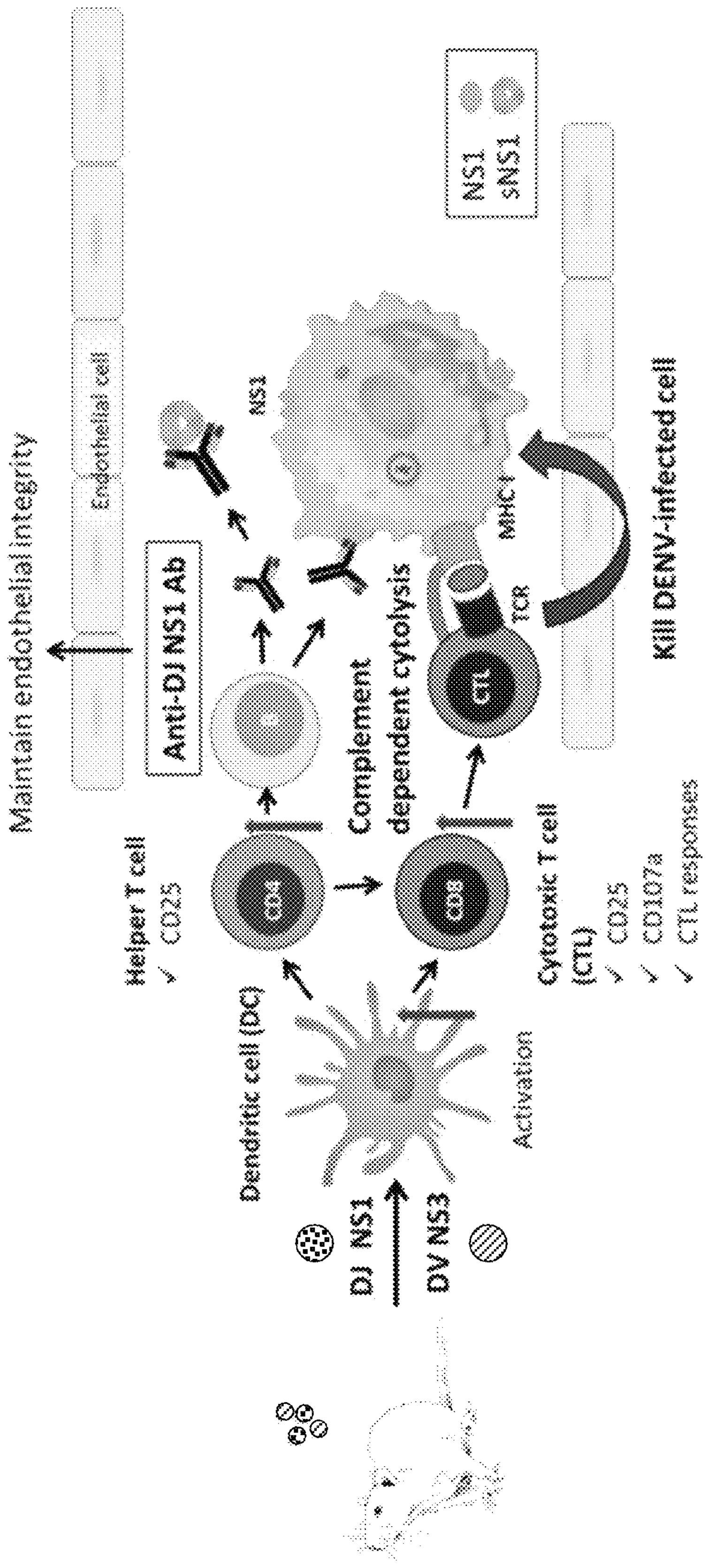
FIG. 19 depicts a schematic model of immune responses and protective effects induced by active immunization with DJ NS1 and NS3. The incorporation of DJ NS1 and NS3 proteins for immunization can synergistically induce more effective immune responses as demonstrated by generating NS3-specific CTL responses and high CD107a expression, as well as promoting NS1-specific T cell responses and antibody titers. The protective mechanisms include direct killing of DENV-infected cells by CTLs and neutralization of NS1-induced pathogenic effects by anti-NS1 antibodies.
Figure 20A:
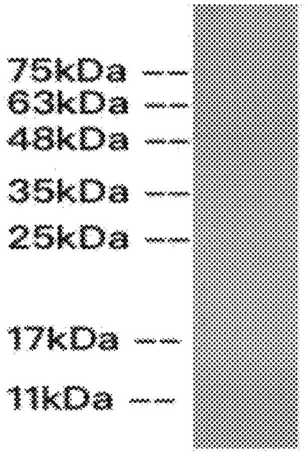
FIGS. 20A to 20D depicts expression levels of truncated NS1ΔC-cEDIII-truncated NS3c fusion protein (FIGS. 20A and 20B, MW=49 kDa) and truncated NS1ΔC-truncated NS3c fusion protein (FIGS. 20C and 20D, MW=35 kDa) detected by SDS-PAGE (FIGS. 20A and 20C) and Western blotting (FIGS. 20B and 20D) according to several embodiments of the present invention.
Figure 20B:
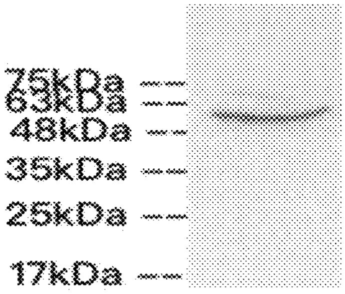
Figure 20C:
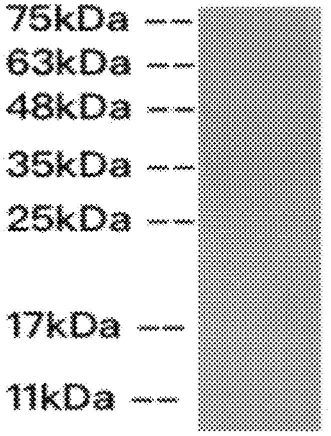
Figure 20D:
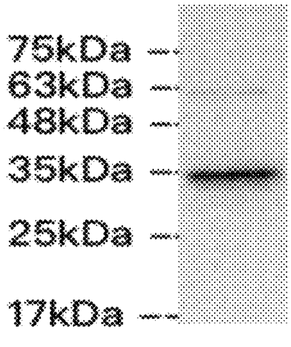

In those examples, modified NS1 combined with NS3 was used in a novel vaccine strategy and investigated the mechanisms of the observed protective effects against DENV in mice. Non-replicating recombinant protein-based subunit vaccines are considered to be safer and can be easily reformulated. In an effort to solve a common problem for subunit vaccine, namely that certain highly purified antigens are poorly immunogenic, the example combined NS1 protein with immunodominant NS3 protein. Results show that NS3 protein can synergistically induce more effective immune responses including not only generating NS3-specific CTL responses, but also promoting NS1-specific T cell responses and antibody titers. Active immunization with DJ NS1 plus NS3 exhibited better performance in both immune responses and protection compared to DJ NS1 alone or NS3 alone (FIG. 19).

The Protective Effects Provided by Immunization with Recombinant NS1fΔC-cEDIII-NS3cf and NS1fΔC-NS3cf Proteins Against DENV Infection are Determined In Vitro by FRNT and CDC and In Vivo by Mouse Tail Bleeding Time.

As aforementioned, DENV NS3-induced $CD8^+$ T cell responses were shown to be protective against heterotypic DENV re-infection, thus reduce the risk of antibody-dependent enhancement (ADE). Therefore, the fusion proteins with cEDIII, NS1ΔC and NS3 were also evaluated as candidate for vaccine development. NS1fΔC-cEDIII-NS3cf and NS1fΔC-NS3cf proteins were expressed by mammalian 293F cells (Table 3) and *Drosophila* S2 cells (Table 4). C3H/HeN mice were s.c. immunized with 25 μg of NS1fΔC-cEDIII-NS3cf or NS1fΔC-NS3cf proteins for three times using alum as the adjuvant. Mouse sera were collected after second and third immunization, and the antibody titers against DJ NS1, NS3 and cEDIII were determined (Tables 3 and 4). The NS1fΔC-NS3cf fusion protein could stimulate relatively higher antibody titers than the NS1fΔC-cEDIII-NS3cf fusion protein with the third immunization in mice.

TABLE 3

| Antibody titers (×$10^3$) | | | | | |
|---|---|---|---|---|---|
| Immunization | | 25 μg His-NS1fΔC-cEDIII-NS3cf-His | | 25 μg His-NS1fΔC-NS3cf-His | |
| Times of Immunization | | $2^{nd}$ | $3^{rd}$ | $2^{nd}$ | $3^{rd}$ |
| Anti-DJ NS1 | IgM | $2^2$ | $2^4$ | $2^2$ | $2^6$ |
| | IgG | $2^1$ | $2^2$ | $2^1$ | $2^3$ |
| Anti-NS3 | IgM | $2^3$ | $2^3$ | $2^2$ | $2^6$ |
| | IgG | $2^2$ | $2^3$ | $2^1$ | $2^3$ |
| Anti-cEDIII | IgM | N.D. | $2^2$ | | |
| | IgG | N.D. | $2^2$ | | |

TABLE 4

| Antibody titers (×$10^3$) | | | | | |
|---|---|---|---|---|---|
| Immunization | | 25 uni His-NS1fΔC-cEDIII-NS3cf-Strep | | 25 un His-NS1fΔC-NS3cf-Strep | |
| Times of Immunization | | $2^{nd}$ | $3^{rd}$ | $2^{nd}$ | $3^{rd}$ |
| Anti-DJ NS1 | IgM | $2^3$ | $2^5$ | $2^3$ | $2^4$ |
| | IgG | $2^3$ | $2^5$ | $2^3$ | $2^6$ |
| Anti-NS3 | IgM | $2^3$ | $2^5$ | $2^2$ | $2^4$ |
| | IgG | $2^3$ | $2^5$ | $2^2$ | $2^5$ |
| Anti-cEDIII | IgM | $2^2$ | $2^4$ | | |
| | IgG | $2^2$ | $2^4$ | | |

Figure 21A:
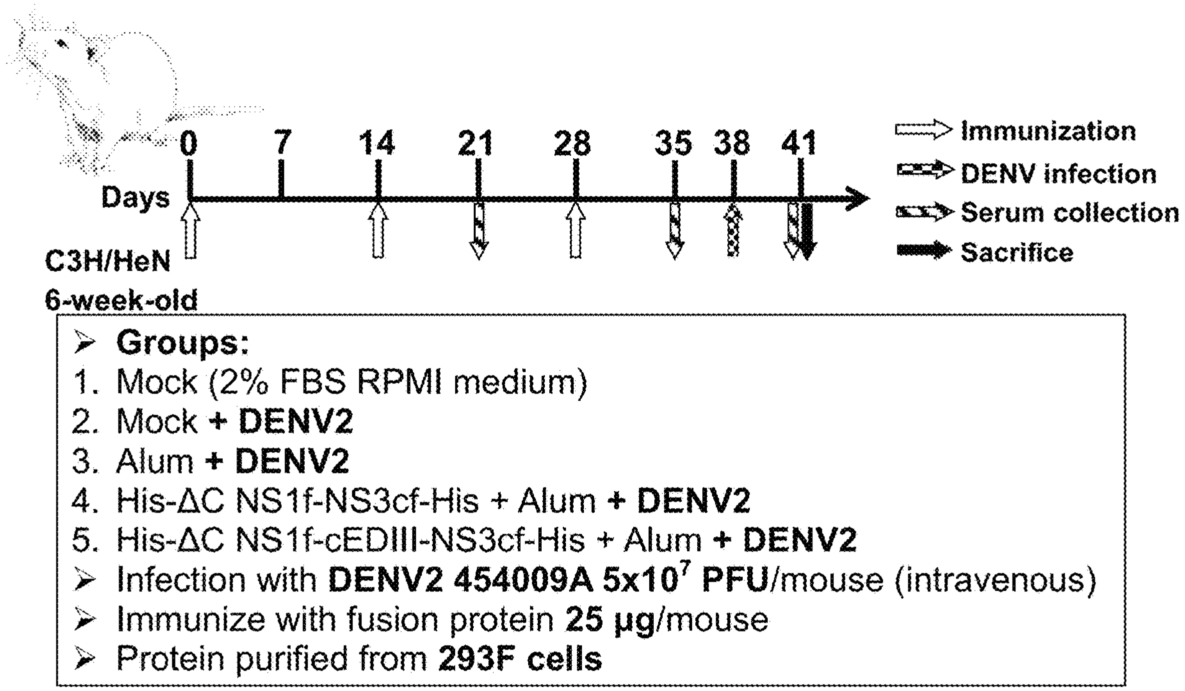
FIGS. 21A to 21D depicts experimental design (FIG. 21A) and the results (FIGS. 21B to 21D) of active immunization with truncated NS1ΔC-cEDIII-truncated NS3c (or called as NS1fΔC-cEDIII-NS3cf) fusion protein and truncated NS1ΔC-truncated NS3c (or called as NS1fΔC-NS3cf) fusion protein both purified from mammalian 293F cells, for reducing viral titers (FIG. 21B), complement-dependent cytotoxicity (CDC.
Figure 21B:
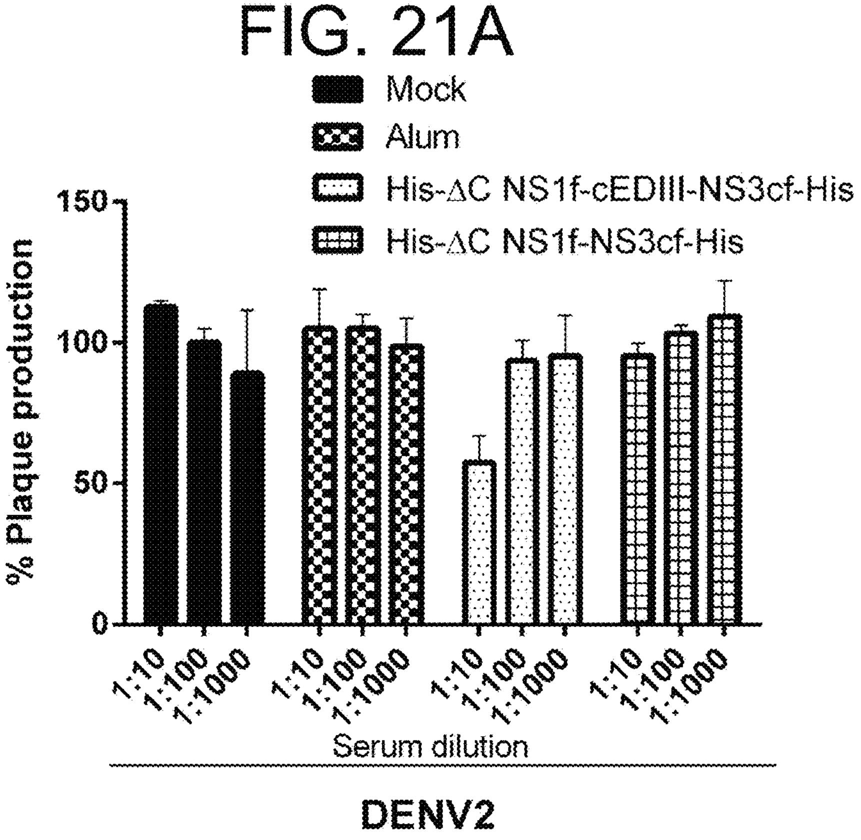
Figure 22A:
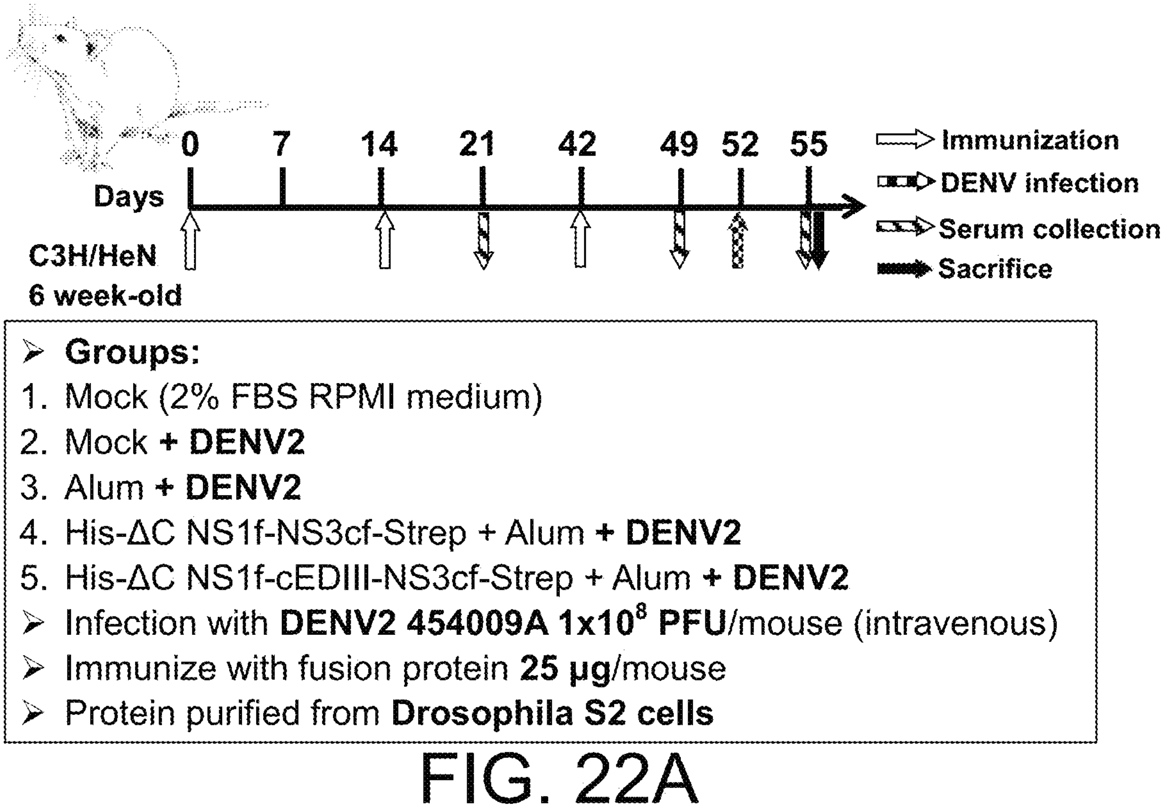
FIGS. 22A to 22D depicts experimental design (FIG. 22A) and the results (FIGS. 22B to 22D) of active immunization with truncated NS1ΔC-cEDIII-truncated NS3c (or called as NS1fΔC-cEDIII-NS3cf) fusion protein and truncated NS1ΔC-truncated NS3c (or called as NS1fΔC-NS3cf) fusion protein both purified from *Drosophila* S2 cells, for reducing viral titers (FIG. 22B), complement-dependent cytotoxicity (CDC.
Figure 22B:
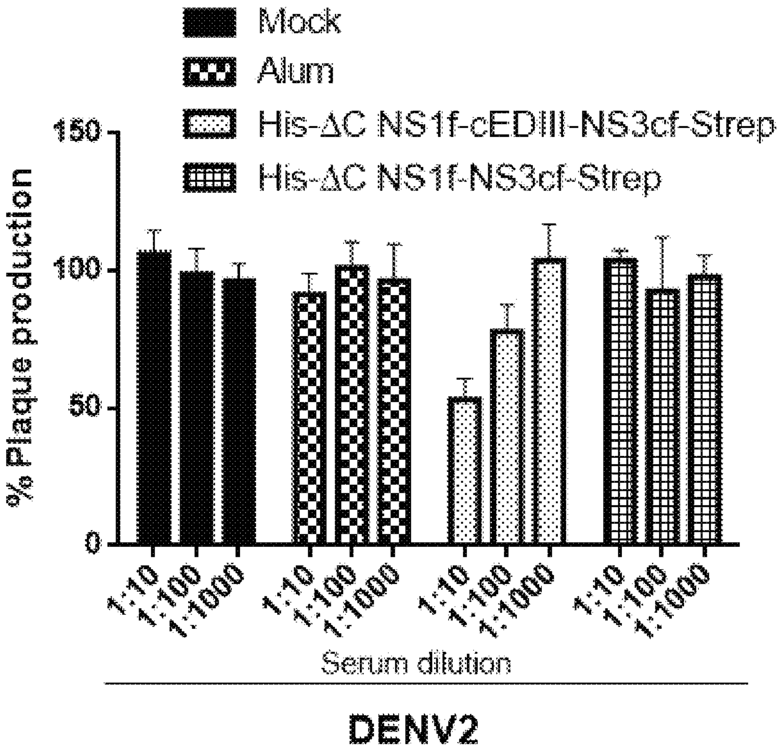

To validate the neutralization capacity of immunized mouse serum, we conducted a focus reduction neutralization test (FRNT). Ten-fold serum dilutions of mock serum, alum alone-immunized serum, NS1fΔC-cEDIII-NS3cf-immunized serum and NS1fΔC-NS3cf-immunized serum were mixed with DENV2, and then added to BHK-21 cells which were seeded on a 96-well μlate. The group of NS1fΔC-cEDIII-NS3cf-immunized mouse serum, but not NS1fΔC-NS3cf-immunized serum, alum-immunized serum or mock control serum, neutralized DENV (FIGS. 21B and 22B).

Figure 21C:
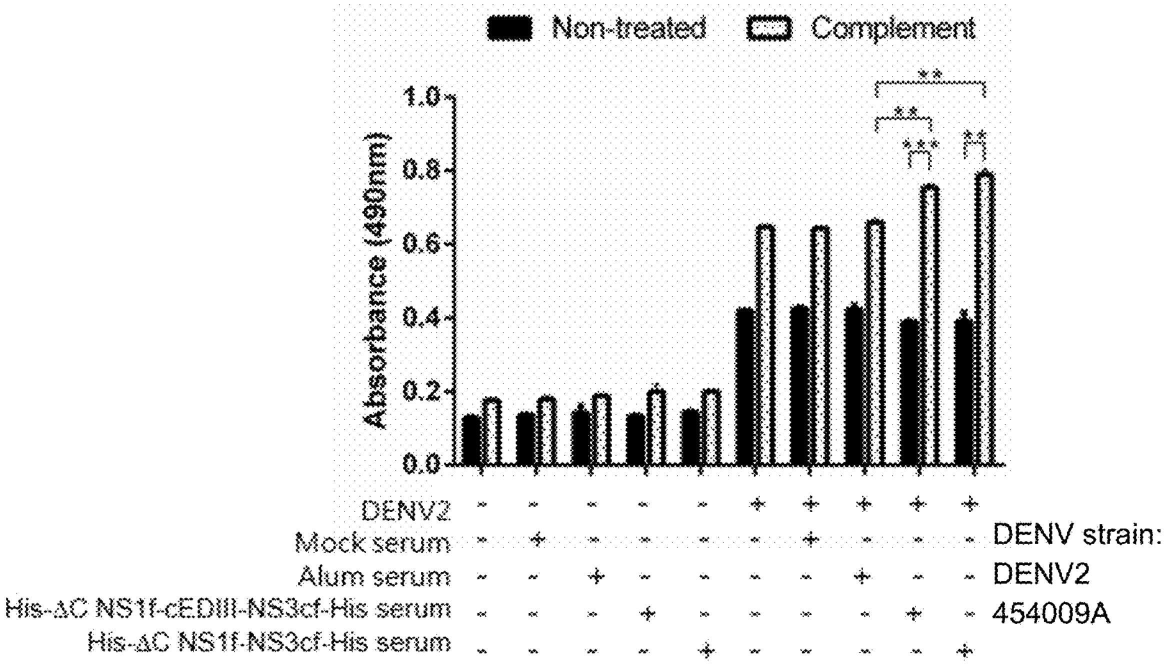
Figure 22C:
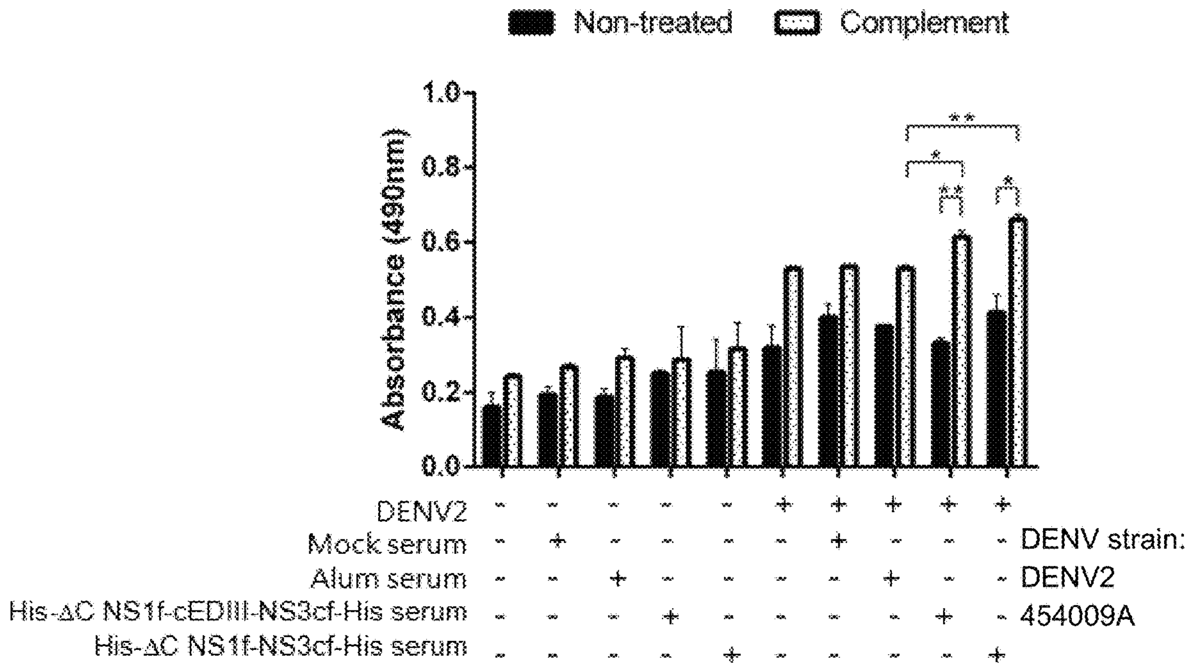

NS1 is expressed on the surface of infected cells. The inventors wondered whether the NS1fΔC-cEDIII-NS3cf- and NS1fΔC-NS3cf-immunized mouse serum containing anti-AC NS1 antibodies could cause complement-mediated cytolysis on DENV-infected cells. Huh-7 cells seeded in 96-well plates were infected by DENV2. Then, cells were incubated with 1:20 dilution of mock serum, alum alone-immunized serum, NS1fΔC-cEDIII-NS3cf-immunized serum or NS1fΔC-NS3cf-immunized serum with or without complement. Cytolysis was measured by the release of LDH. Both NS1fΔC-cEDIII-NS3cf- and NS1fΔC-NS3cf-immunized mouse sera mixed with complement caused cytolysis on DENV-infected cells as compared to other groups (FIGS. 21C and 22C).

Figure 21D:
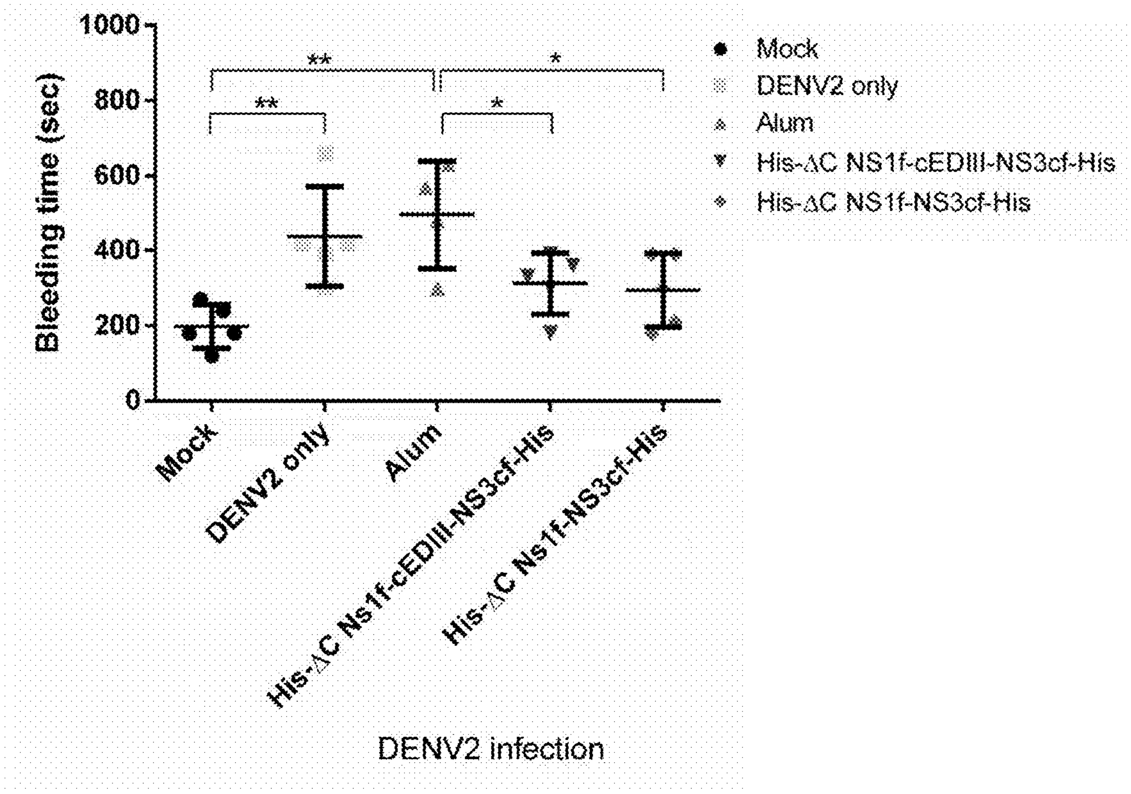
Figure 22D:
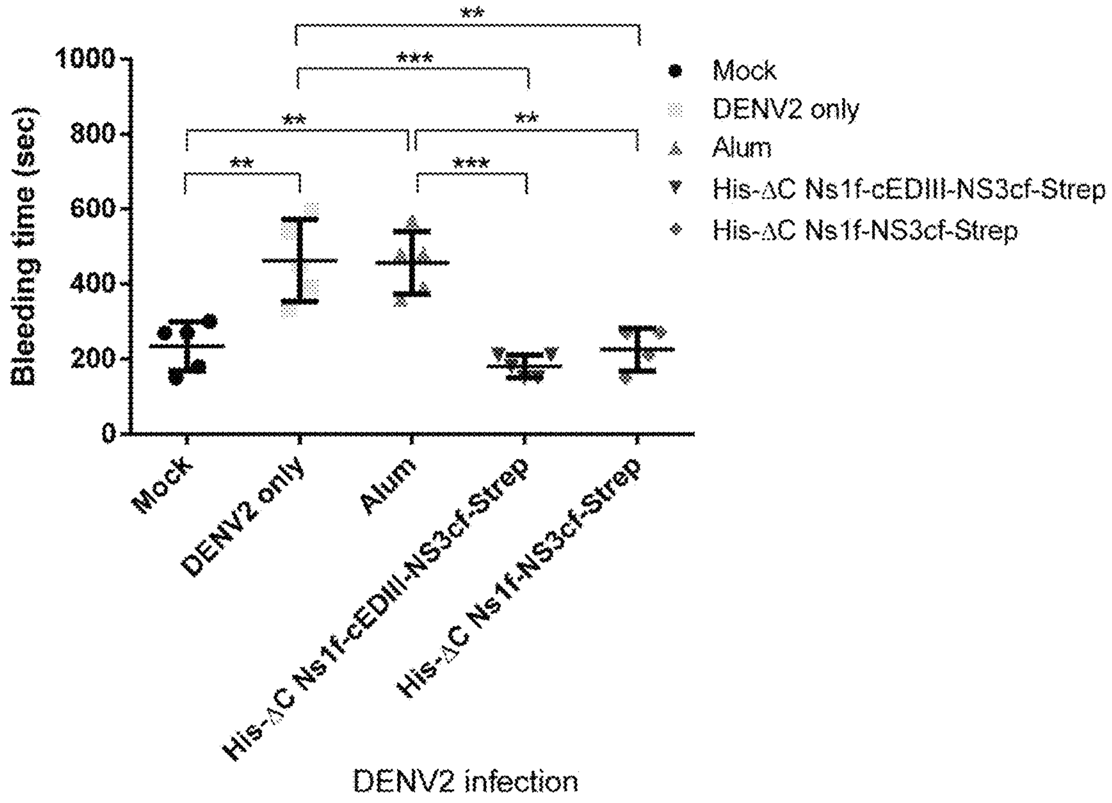

Then, the inventors tested the protective effect provided by immunization with NS1fΔC-cEDIII-NS3cf and NS1fΔC-NS3cf proteins of which mice were i.v. inoculated with DENV. Results showed that the NS1fΔC-cEDIII-NS3cf- and NS1fΔC-NS3cf-immunized mice displayed lower mouse-tail bleeding time induced by DENV as compared with mice infected with DENV only or DENV plus alum (FIGS. 21D and 22D).

Previous studies showed that Th1-biased responses dominated by IFN-γ are associated with less severe secondary DENV infection, while T cell production of TNFα is associated with more severe infection. Other studies have confirmed that the recombinant DENV2 NS3 protein induced Th1 responses with a higher IFN-γ/TNFα. However, a previous clinical study demonstrated the association of robust T cell responses with dengue hemorrhagic fever (DHF), particularly against NS3. This discrepancy needs to be further investigated. In the study of the inventors, active immunization with DJ NS1 plus NS3 induces CD107a expression on the surface of $CD8^+$ T cells in response to DJ NS1 stimulation, revealing that combination of DJ NS1 with NS3 promotes development of cytotoxic activity against DJ NS1. In agreement with the results from CTL assay, active immunization with DJ NS1 plus NS3 induced cytotoxicity against not only NS3-expressing L929 but also DJ NS1-expressing L929 cells. A previous study indicated that the concomitant production of IFN-γ and CD107a expression with newly synthesis of perforin protein can promote cytotoxicity in antigen-specific $CD8^+$ T cells. However, the detailed mechanisms of cytotoxic action remain to be elucidated.

Since active immunization with NS3 also induces high titers of anti-NS3 IgM and IgG, the example cannot exclude the possible role of anti-NS3 antibodies in this infection model. Previous studies showed the protective effects by antibodies directed against NS3. Although anti-NS3 antibodies, which are not neutralizing antibodies, have been detected in sera of patients with primary and secondary DENV infection, the role of anti-NS3 antibodies remains to be further investigated.

The clinical symptoms of DENV infection range from asymptomatic, classic dengue fever to severe life-threatening DHF, which are mainly characterized by increased vascular leakage leading to hemorrhage, hypovolemia, hypotension, and also shock syndrome. In this DENV infection model, mice presented with viremia, prolonged bleeding time, vascular change, and hemorrhage. Prolonged bleeding time may reflect coagulation abnormalities including thrombocytopenia and disruption of the coagulation system. In adults, platelet counts are significantly associated with bleeding manifestations of DENV infection. The mechanisms involved in thrombocytopenia and bleeding during DENV infection are not fully understood, although several hypotheses have been suggested. In this DENV infection model, active immunization with either DJ NS1 or NS3 can shorten DENV-associated prolonged bleeding time (FIG. 18B). DJ NS1 induces NS1 neutralizing antibodies which directly block the pathogenesis of sNS1 (data not shown) and also cause complement-mediated cytolysis with anti-NS1 antibodies against DENV-infected cells (Wan et al., 2017). On the other hand, active immunization with NS3 induces NS3-specific CTL to reduce viral titers as well as sNS1 levels in serum to shorten the prolonged bleeding time. Collectively, active immunization with DJ NS1 plus NS3 can significantly shorten DENV-associated prolonged bleeding time through multiple mechanisms.

The pathogenesis of and protection against vascular leakage and hemorrhage are complex. sNS1 can direct complement against endothelial cells and induce endothelial cell apoptosis (Amorim et al., 2014). Recent studies showed that sNS1 can bind to TLR4 and then lead to cell release of proinflammatory cytokines which contribute to vascular leakage (Modhiran et al., 2015). sNS1 has also been shown to activate TLR2 and TLR6, leading to increased proinflammatory cytokine production (Chen et al., 2015). In addition, macrophage migration inhibitory factor induced by DENV infection or NS1 may enhance DENV replication through autophagy, which may also contribute to vascular leakage by disrupting endothelial cell tight junctions both in humans and in mice (Chen et al., 2018; Chuang et al., 2011; Chen et al., 2016). NS1 can also directly disrupt the endothelial glycocalyx leading to hyperpermeability (Puerta-Guardo et al., 2016; Chen et al., 2018). Thus, sNS1 can be a major factor directly or indirectly contributing to vascular leakage and hemorrhage. As shown in the results, active immunization with DJ NS1 alone or DJ NS1 plus NS3 significantly prevented DENV-associated vascular permeability change. In contrast, active immunization with NS3 alone did not prevent vascular change. These results highlight the essential roles of NS1 neutralizing antibodies in preventing vascular leakage and hemorrhage.

Based on clinical observations that dengue disease is more severe in secondary heterotypic infections, any successful vaccine would need to induce a protective and durable immune response to all four DENV serotypes simultaneously to avoid ADE (Pang et al., 2017). The vaccine candidate, DJ NS1 plus NS3, will not cause ADE. Moreover, the example have demonstrated that active immunization with DJ NS1 plus NS3 induced specific $CD8^+$ T cell responses, which recently were shown to be able to be protective against heterotypic DENV re-infection. Following an emerging Zika virus (ZIKV) infection, several studies showed that previous DENV infection can cause ADE of ZIKV infection by DENV-specific antibodies. On the other hand, another embodiment demonstrated that five DENV-epitope-specific $CD8^+$ T cells confer cross-protection against subsequent ZIKV infection (Wen et al., 2017). The candidate vaccine NS3 component contains one of the five epitopes, which can mediate cross-protection against subsequent ZIKV infection, and may avoid ADE of ZIKV. However, cross-protection against ZIKV infection provided by the vaccine candidate needs to be further investigated.

In conclusion, the present invention explores a novel DENV vaccine strategy combining cEDIII-NS1ΔC fusion protein and NS3 protein which provides enhanced protection against DENV challenge and associated pathological effects.

Although the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, the spirit and claim scope should not be limited to the description of the exemplified embodiments demonstrated above.

REFERENCES

Adikari T N, Gomes L, Wickramasinghe N, Salimi M, Wijesiriwardana N, Kamaladasa A, Shyamali N L A, Ogg G S, Malavige G N. Dengue NS1 antigen contributes to disease severity by inducininterleukin (IL)-10 by monocytes. Clin Exp Immunol. 2016; 184(1):90-100.

Amorim J H, Alves R P, Boscardin S B, Ferreira L C. The dengue virus non-structural 1 protein: risks and benefits. Virus Res. 2014; 181:53-60.

Beatty P R, Puerta-Guardo H, Killingbeck S S, Glasner D R, Hopkins K, Harris E. Dengue virus NS1 triggers endothelial permeability and vascular leak that is prevented by NS1 vaccination. Sci Transl Med. 2015; 7:304ra141.

Bhatt S, Gething P W, Brady O J, Messina J P, Farlow A W, Moyes C L, Drake J M, Brownstein J S, Hoen A G, Sankoh O, Myers M F, George D B, Jaenisch T, Wint G R W, Simmons C P, Scott T W, Farrar J J, Hay S I. The global distribution and burden of dengue. Nature. 2013, 496(7446):504-7.

Biswal S, Reynales H, Saez-Llorens X, Lopez P, Borja-Tabora C, Kosalaraksa P, Sirivichayakul C, Watanaveeradej V, Rivera L, Espinoza F, Fernando L, Dietze R, Luz K, da Cunha R V, Jimeno J, Lopez-Medina E, Borkowski A, Brose M, Rauscher M, LeFevre I, Bizjajeva S, Bravo L, Wallace D, for the TIDES Study Group. Efficacy of a tetravalent dengue vaccine in healthy children and adolescents. N Engl J Med. 2019; 381:2009-19.

Chao C H, Wu W C, Lai Y C, Tsai P J, Perng G C, Lin Y S, Yeh T M. Dengue virus nonstructural protein 1 activates platelets via Toll-like receptor 4, leading to thrombocytopenia and hemorrhage. PLoS Pathog. 2019, 15(4): e1007625.

Chen C L, Lin C F, Wan S W, Wei L S, Chen M C, Yeh T M, Liu H S, Anderson R, Lin Y S. Anti-dengue virus nonstructural protein 1 antibodies cause NO-mediated endothelial cell apoptosis via ceramide-regulated GSK-3b and NF-kB activation. J Immunol. 2013; 191:1744-52.

Chen H R, Chao C H, Liu C C, Ho T S, Tsai H P, Perng G C, Lin Y S, Wang J R, Yeh T M. Macrophage migration inhibitory factor is critical for dengue NS1-induced endothelial glycocalyx degradation and hyperpermeability. PLoS Pathog. 2018; 14(4):e1007033.

Chen H R, Chuang Y C, Lin Y S, Liu H S, Liu C C, Perng G C, Yeh T M. Dengue virus nonstructural protein 1 induces vascular leakage through macrophage migration inhibitory factor and autophagy. PLoS Negl Trop Dis. 2016, 10(7):e0004828.

Chen H W, Liu S J, Li Y S, Liu H H, Tsai J P, Chiang C Y, Chen M Y, Hwang C S, Huang C C, Hu H M, Chung H H, Wu S H, Chong P, Leng C H, Pan C H. A consensus envelope protein domain III can induce neutralizing antibody responses against serotype 2 of dengue virus in non-human primates. Arch Virol. 2013, 158(7):1523-31.

Chen J, Ng M M, Chu J J. Activation of TLR2 and TLR6 by dengue NS1 protein and its implications in the immunopathogenesis of dengue virus infection. PLoS Pathog. 2015, 11:e1005053.

Chen M C, Lin C F, Lei H Y, Lin S C, Liu H S, Yeh T M, Anderson R, Lin Y S. Deletion of the C-terminal region of dengue virus nonstructural protein 1 (NS1) abolishes anti-NS1-mediated platelet dysfunction and bleeding tendency. J Immunol. 2009, 183(3):1797-803.

Cheng H J, Lin C F, Lei H Y, Liu H S, Yeh T M, Luo Y H, Lin Y S. Proteomic analysis of endothelial cell autoantigens recognized by anti-dengue virus nonstructural protein 1 antibodies. Exp Biol Med. (Maywood) 2009; 234 (1):63-73.

Chin J F, Chu J J, Ng M L. The envelope glycoprotein domain III of dengue virus serotypes 1 and 2 inhibit virus entry. Microbes Infect. 2007; 9(1):1-6.

Chuang Y C, Lei H Y, Liu H S, Lin Y S, Fu T F, Yeh T M. Macrophage migration inhibitory factor induced by dengue virus infection increases vascular permeability. Cytokine. 2011; 54:222-31.

Coller B A, Clements D E, Bett A J, Sagar S L, Ter Meulen J H. The development of recombinant subunit envelope-based vaccines to protect against dengue virus induced disease. Vaccine. 2011; 29(42):7267-75.

Diamond M S, Pierson T C. Molecular insight into dengue virus pathogenesis and its implications for disease control. Cell. 2015, 162(3):488-92.

Flamand M, Megret F, Mathieu M, Lepault J, Rey F A, Deubel V. Dengue virus type 1 nonstructural glycoprotein NS1 is secreted from mammalian cells as a soluble hexamer in a glycosylation-dependent fashion. J Virol. 1999; 73(7):6104-10.

Glasner D R, Puerta-Guardo H, Beatty P R, Harris E. The good, the bad, and the shocking: The multiple roles of dengue virus nonstructural protein 1 in protection and pathogenesis. Annu Rev Virol. 2018; 5:227-53.

Gromowski G D, Barrett A D. Characterization of an antigenic site that contains a dominant, type-specific neutralization determinant on the envelope protein domain III (ED3) of dengue 2 virus. Virology. 2007; 366(2):349-60.

Gubler D J, Halstead S B. Is Dengvaxia® a useful vaccine for dengue endemic areas? BMJ. 2019; 367:15710.

Guzman M G, Harris E. Dengue. Lancet. 2015; 385:453-65.

Guzman M G, Hermida L, Bernardo L, Ramirez R, Guillen G. Domain III of the envelope protein as a dengue vaccine target. Expert Rev Vaccines. 2010; 9(2):137-47.

Halstead S B. Identifying protective dengue vaccines: guide to mastering an empirical process. Vaccine. 2013; 31(41): 4501-7.

Kao Y S, Yu C Y, Huang H J, Tien S M, Wang W Y, Yang M, Anderson R, Yeh T M, Lin Y S, Wan S W. Combination of Modified N S1 and NS3 as a Novel Vaccine Strategy against Dengue Virus Infection. J Immunol. 2019; 203:1909-17.

Katzelnick L C, Coloma J, Harris E. Dengue: Knowledge gaps, unmet needs and research priorities. Lancet Infect Dis. 2017, 17(3):e88-e100.

Kirkpatrick B D, Durbin A P, Pierce K K, Carmolli M P, Tibery C M, Grier P L, Hynes N, Diehl S A, Elwood D, Jarvis A P, Sabundayo B P, Lyon C E, Larsson C J, Jo M, Lovchik J M, Luke C J, Walsh M C, Fraser E A, Subbarao K, Whitehead S S. Robust and balanced immune responses to all 4 dengue virus serotypes following administration of a single dose of a live attenuated tetravalent dengue vaccine to healthy, flavivirus-naive adults. J Infect Dis. 2015; 212:702-10.

Klein D E, Choi J L, Harrison S C. Structure of a dengue virus envelope protein late-stage fusion intermediate. J Virol. 2013; 87(4):2287-93.

Kuhn R J, Zhang W, Rossmann M G, Pletnev S V, Corver J, Lenches E, Strauss J H. Structure of dengue virus: implications for flavivirus organization, maturation, and fusion. Cell. 2002, 108(5):717-25.

Leng C H, Liu S J, Tsai J P, Li Y S, Chen M Y, Liu H H, Lien S P, Yueh A, Hsiao K N, Lai L W, Liu F C, Chong P, Chen H W. A novel dengue vaccine candidate that induces cross-neutralizing antibodies and memory immunity. Microbes Infect. 2009; 11(2):288-95.

Lin C F, Chiu S C, Hsiao Y L, Wan S W, Lei H Y, Shiau A L, Liu H S, Yeh T M, Chen S H, Liu C C, Lin Y S. Expression of cytokine, chemokine, and adhesion molecule during endothelial cell activation induced by antibodies against dengue virus nonstructural protein 1. J Immunol. 2005; 174:395-403.

Lin C F, Lei H Y, Liu C C, Liu H S, Yeh T M, Wang S T, Yang T I, Sheu F C, Kuo C F, Lin Y S. Generation of IgM anti-platelet autoantibody in dengue patients. J Med Virol. 2001, 63(2):143-9.

Lin C F, Lei H Y, Shiau A L, Liu C C, Liu H S, Yeh T M, Chen S H, Lin Y S. Antibodies from dengue patient sera cross-react with endothelial cells and induce damage. J Med Virol. 2003; 69(1):82-90.

Lin Y S, Yeh T M, Lin C F, Wan S W, Chuang Y C, Hsu T K, Liu H S, Liu C C, Anderson R, Lei H Y. Molecular mimicry between virus and host and its implications for dengue disease pathogenesis. Exp Biol Med. (Maywood) 2011, 236(5):515-23.

Malavige G N, Ogg G S. Pathogenesis of vascular leak in dengue virus infection. Immunology. 2017, 151(3):261-9.

Modhiran N, Watterson D, Muller D A, Panetta A K, Sester D P, Liu L, Hume D A, Stacey K J, Young P R. Dengue virus NS1 protein activates cells via Toll-like receptor 4 and disrupts endothelial cell monolayer integrity. Sci Transl Med. 2015, 7(304):304ra142.

Muller D A, Young P R. The flavivirus NS1 protein: molecular and structural biology, immunology, role in pathogenesis and application as a diagnostic biomarker. Antiviral Res. 2013, 98(2):192-208.

Normile D. Safety concerns derail dengue vaccination program. Science. 2017; 358:1514-5.

Pang E L, Loh H S. Towards development of a universal dengue vaccine—how close are we? Asian Pac J Trop Med. 2017; 10:220-8.

Puerta-Guardo H, Glasner D R, Harris E. Dengue virus NS1 disrupts the endothelial glycocalyx, leading to hyperpermeability. PLoS Pathog. 2016; 12(7):e1005738.

Screaton G, Mongkolsapaya J, Yacoub S, Roberts C. New insights into the immunopathology and control of dengue virus infection. Nat Rev Immunol. 2015; 15(12):745-59.

Sridhar S, Luedtke A, Langevin E, Zhu M, Bonaparte M, Machabert T, Savarino S, Zambrano B, Moureau A, Khromava A, Moodie Z, Westling T, Mascarenas C, Frago C, Cortes M, Chansinghakul D, Noriega F, Bouckenooghe A, Chen J, Ng S P, Gilbert P B, Gurunathan S, Diaz-Granados C A. Effect of dengue serostatus on dengue vaccine safety and efficacy. N Engl J Med. 2018:379:327-40.

Wahala W M, Kraus A A, Haymore L B, Accavitti-Loper M A, de Silva A M. Dengue virus neutralization by human immune sera: role of envelope protein domain III-reactive antibody. Virology. 2009, 392(1):103-13.

Wan S W, Chen P W, Chen C Y, Lai Y C, Chu Y T, Hung C Y, Lee H, Wu H F, Chuang Y C, Lin J, Chang C P, Wang S, Liu C C, Ho T S, Lin C F, Lee C K, Wu-Hsieh B A, Anderson R, Yeh T M, Lin Y S. Therapeutic effects of monoclonal antibody against dengue virus NS1 in a STAT1 knockout mouse model of dengue infection. J Immunol. 2017; 199:2834-44.

Wan S W, Lin C F, Chen M C, Lei H Y, Liu H S, Yeh T M, Liu C C, Lin Y S. C-terminal region of dengue virus nonstructural protein 1 is involved in endothelial cell cross-reactivity via molecular mimicry. Am J Infect Dis. 2008; 4(1):85-91.

Wan S W, Lin C F, Wang S, Chen Y H, Yeh T M, Liu H S, Anderson R, Lin Y S. Current progress in dengue vaccines. J Biomed Sci. 2013; 20:37.

Wan S W, Lu Y T, Huang C H, Lin C F, Anderson R, Liu H S, Yeh T M, Yen Y T, Wu-Hsieh B A, Lin Y S. Protection against dengue virus infection in mice by administration of antibodies against modified nonstructural protein 1. PLoS One. 2014; 9(3):e92495.

Wen J, Elong Ngono A, Regla-Nava J A, Kim K, Gorman M J, Diamond M S, Shresta S. Dengue virus-reactive $CD8^+$ T cells mediate cross-protection against subsequent Zika virus challenge. Nat Commun. 2017; 8:1459.

Wichmann O, Vannice K, Asturias E J, de Albuquerque Luna E J, Longini I, Lopez A L, Smith P G, Tissera H, Yoon I K, Hombach J. Live-attenuated tetravalent dengue vaccines: the needs and challenges of post-licensure evaluation of vaccine safety and effectiveness. Vaccine. 2017; 35:5535-42.

World Health Organization. Dengue vaccine: WHO position paper—July 2016. Wkly Epidemiol Rec. 2016; 91(30):349-64.

What is claimed is:

1. An immunogenic composition [of subunit dengue vaccine], comprising:

a fusion protein of truncated NS1 polypeptide of SEQ ID NOs: 5 and truncated NS3c polypeptide of SEQ ID NOs: 6, and optionally together with one or more pharmaceutically acceptable carriers and/or adjuvants.

2. The immunogenic composition according to claim 1, wherein the fusion protein is in an order of truncated NS1-truncated NS3c from N-terminus to C-terminus.

3. The immunogenic composition according to claim 2, wherein the fusion protein includes a first linker between the truncated NS1 and the truncated NS3c polypeptide.

4. The immunogenic composition according to claim 1, wherein the fusion protein is in an order of truncated NS3c-truncated NS1 from N-terminus to C-terminus.

5. The immunogenic composition according to claim 4, wherein the fusion protein includes a first linker between the truncated NS1 polypeptide and the truncated NS3c polypeptide.

6. The immunogenic composition according to claim 1, further comprising a cEDIII polypeptide listed as SEQ ID NOs: 1 or 4.

7. The immunogenic composition according to claim 6, wherein the truncated NS1 polypeptide of the fusion protein is conjugated to the cEDIII polypeptide.

8. The immunogenic composition according to claim 6, wherein the truncated NS3c polypeptide of the fusion protein is conjugated to the cEDIII polypeptide.

9. The immunogenic composition according to claim 6, wherein the cEDIII polypeptide is conjugated between the truncated NS1 polypeptide and the truncated NS3c polypeptide.

* * * * *